(12) United States Patent
Brumback et al.

(10) Patent No.: US 9,017,221 B2
(45) Date of Patent: Apr. 28, 2015

(54) DELAYED GOAL CELEBRATION

(71) Applicant: Fitbit, Inc., San Francisco, CA (US)

(72) Inventors: Christine Boomer Brumback, San Francisco, CA (US); David Wayne Knight, San Francisco, CA (US); Jayson Dean Michilena Messenger, San Francisco, CA (US); Jung Ook Hong, Emeryville, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/261,349

(22) Filed: Apr. 24, 2014

(65) Prior Publication Data

US 2015/0094832 A1    Apr. 2, 2015

Related U.S. Application Data

(62) Division of application No. 14/050,182, filed on Oct. 9, 2013.

(60) Provisional application No. 61/886,017, filed on Oct. 2, 2013.

(51) Int. Cl.
*A63B 23/00* (2006.01)
*A63B 24/00* (2006.01)
(Continued)

(52) U.S. Cl.
CPC ......... *A63B 24/0062* (2013.01); *A63B 2220/74* (2013.01); *G01C 22/006* (2013.01); *A61B 5/7282* (2013.01); *A61B 2503/12* (2013.01); *A61B 2503/10* (2013.01); *A61B 5/7455* (2013.01); *A61B 5/746* (2013.01); *A61B 5/6895* (2013.01); *A61B 5/6801* (2013.01); *A61B 5/742* (2013.01); *A63B 2230/65* (2013.01); *A61B 5/02438* (2013.01); *A63B 2230/205* (2013.01); *A63B 2230/50* (2013.01); *A63B 2230/202* (2013.01); *A63B 2230/207* (2013.01); *A63B 2230/04* (2013.01); *A63B 2225/50* (2013.01); *A63B 2230/01* (2013.01);
(Continued)

(58) Field of Classification Search
None
See application file for complete search history.

(56) References Cited

U.S. PATENT DOCUMENTS 4,938,228 A    7/1990   Righter et al.
5,876,350 A    3/1999   Lo et al.
(Continued)

FOREIGN PATENT DOCUMENTS

EP    1 721 237         8/2012
WO   WO 2013/040674   3/2013
(Continued)

OTHER PUBLICATIONS

Zichermann, G. & Cunningham, C. Gamification by Design. (O'Reilly Media, 2011).*
(Continued)

*Primary Examiner* — Soren Harward
(74) *Attorney, Agent, or Firm* — Weaver Austin Villeneuve & Sampson

(57) ABSTRACT

A biometric monitoring device with a display is provided. The biometric monitoring device may track the completion progress towards one or more biometric performance goals and provide a goal celebration indicator upon completion of a biometric performance goal and subsequent receipt of an input signal. In some implementations, the completion of a biometric performance goal may be signaled prior to receipt of the input signal using a secondary indicator.

27 Claims, 12 Drawing Sheets

(51) Int. Cl.
*A61B 5/00* (2006.01)
*G01C 22/00* (2006.01)
*A61B 5/024* (2006.01)

(52) U.S. Cl.
CPC ........ *A63B 2230/10* (2013.01); *A63B 2220/70* (2013.01); *A63B 2225/20* (2013.01); *A63B 2220/72* (2013.01); *A63B 2220/40* (2013.01); *A63B 2024/0068* (2013.01); *A63B 24/0059* (2013.01)

(56) References Cited

U.S. PATENT DOCUMENTS

| | | |
|---|---|---|
| 5,978,923 A | 11/1999 | Kou |
| 6,583,369 B2 | 6/2003 | Montagnino et al. |
| 6,888,927 B1 | 5/2005 | Cruickshank et al. |
| 7,155,729 B1 | 12/2006 | Andrew et al. |
| 7,559,877 B2 * | 7/2009 | Parks et al. ........... 482/8 |
| 7,662,065 B1 | 2/2010 | Kahn et al. |
| 8,172,761 B1 | 5/2012 | Rulkov et al. |
| 8,306,508 B1 | 11/2012 | Lundy et al. |
| 8,734,296 B1 | 5/2014 | Brumback et al. |
| 8,944,958 B1 | 2/2015 | Brumback et al. |
| 2001/0002122 A1 * | 5/2001 | Vong et al. ........... 340/691.1 |
| 2002/0161644 A1 | 10/2002 | Duffield |
| 2004/0127198 A1 | 7/2004 | Roskind et al. |
| 2005/0250551 A1 | 11/2005 | Helle |
| 2006/0020177 A1 | 1/2006 | Seo et al. |
| 2006/0036642 A1 | 2/2006 | Horvitz et al. |
| 2006/0259537 A1 | 11/2006 | Emberton et al. |
| 2006/0277100 A1 | 12/2006 | Parham |
| 2006/0293041 A1 * | 12/2006 | Kim ........... 455/418 |
| 2007/0118043 A1 | 5/2007 | Oliver et al. |
| 2007/0143068 A1 | 6/2007 | Pasolini et al. |
| 2007/0188468 A1 | 8/2007 | Lee et al. |
| 2007/0219059 A1 | 9/2007 | Schwartz et al. |
| 2008/0070603 A1 | 3/2008 | Mao |
| 2008/0157956 A1 | 7/2008 | Radivojevic et al. |
| 2008/0243432 A1 * | 10/2008 | Kato et al. ........... 702/160 |
| 2008/0249736 A1 | 10/2008 | Prstojevich |
| 2008/0269625 A1 | 10/2008 | Halperin et al. |
| 2008/0319330 A1 | 12/2008 | Juntunen et al. |
| 2009/0043531 A1 | 2/2009 | Kahn et al. |
| 2009/0105047 A1 | 4/2009 | Guidi et al. |
| 2009/0125917 A1 | 5/2009 | Parker et al. |
| 2009/0167542 A1 | 7/2009 | Culbert et al. |
| 2009/0221403 A1 | 9/2009 | Chan et al. |
| 2009/0305732 A1 | 12/2009 | Marcellino et al. |
| 2009/0305744 A1 | 12/2009 | Ullrich |
| 2009/0320047 A1 | 12/2009 | Khan et al. |
| 2010/0015584 A1 | 1/2010 | Singer et al. |
| 2010/0024531 A1 | 2/2010 | Senoo |
| 2010/0076278 A1 | 3/2010 | van der Zande et al. |
| 2010/0105525 A1 | 4/2010 | Thukral et al. |
| 2010/0210975 A1 | 8/2010 | Anthony, III et al. |
| 2010/0331145 A1 | 12/2010 | Lakovic et al. |
| 2010/0331147 A1 * | 12/2010 | Mikan et al. ........... 482/9 |
| 2011/0032105 A1 | 2/2011 | Hoffman et al. |
| 2011/0082007 A1 | 4/2011 | Birrell et al. |
| 2011/0152696 A1 | 6/2011 | Ryan |
| 2011/0213473 A1 | 9/2011 | Vitolo et al. |
| 2012/0010478 A1 | 1/2012 | Kinnunen et al. |
| 2012/0041767 A1 | 2/2012 | Hoffman et al. |
| 2012/0078127 A1 | 3/2012 | McDonald et al. |
| 2012/0112908 A1 | 5/2012 | Prykari et al. |
| 2012/0129138 A1 | 5/2012 | Redmann |
| 2012/0159218 A1 | 6/2012 | Vangala et al. |
| 2012/0246246 A1 | 9/2012 | Moore |
| 2012/0252416 A1 | 10/2012 | Kissinger et al. |
| 2012/0253485 A1 | 10/2012 | Weast et al. |
| 2012/0274508 A1 | 11/2012 | Brown et al. |
| 2012/0277605 A1 | 11/2012 | Colborn |
| 2012/0291544 A1 * | 11/2012 | Kawabe ........... 73/488 |
| 2012/0303319 A1 | 11/2012 | Kirkeby |
| 2013/0013331 A1 | 1/2013 | Horseman |
| 2013/0017891 A1 | 1/2013 | Romero et al. |
| 2013/0067014 A1 | 3/2013 | Lau et al. |
| 2013/0078958 A1 | 3/2013 | Kyprianou |
| 2013/0090881 A1 | 4/2013 | Janardhanan et al. |
| 2013/0106684 A1 | 5/2013 | Weast et al. |
| 2013/0117381 A1 | 5/2013 | Garcia et al. |
| 2013/0122928 A1 * | 5/2013 | Pfluger ........... 455/456.1 |
| 2013/0123959 A1 | 5/2013 | Kan et al. |
| 2013/0138734 A1 | 5/2013 | Crivello et al. |
| 2013/0157646 A1 | 6/2013 | Ferren et al. |
| 2013/0178334 A1 | 7/2013 | Brammer |
| 2013/0205306 A1 | 8/2013 | Kelly |
| 2013/0234924 A1 | 9/2013 | Janefalkar et al. |
| 2013/0237874 A1 | 9/2013 | Zoicas |
| 2013/0241718 A1 | 9/2013 | Wang et al. |
| 2013/0290879 A1 | 10/2013 | Greisson |
| 2013/0293494 A1 | 11/2013 | Reshef |
| 2014/0066816 A1 | 3/2014 | McNames et al. |
| 2014/0099614 A1 * | 4/2014 | Hu et al. ........... 434/236 |

FOREIGN PATENT DOCUMENTS

| | | |
|---|---|---|
| WO | WO 2013/093011 | 6/2013 |
| WO | WO 2013/169755 | 11/2013 |

OTHER PUBLICATIONS

Consolvo, S., Everitt, K., Smith, I. & Landay, J. A. Design requirements for technologies that encourage physical activity. in Human Factors in Computing Systems 457 (ACM Press, 2006). doi:10.1145/1124772.1124840.*
U.S. Appl. No. 14/050,182, filed Oct. 9, 2013, Brumback et al.
U.S. Appl. No. 14/261,344, filed Apr. 24, 2014, Brumback et al.
U.S. Appl. No. 14/261,347, filed Apr. 24, 2014, Brumback et al.
US Office Action, dated Dec. 24, 2013, issued in U.S. Appl. No. 14/050,166.
US Applicant-Initiated Interview Summary dated Mar. 11, 2014, issued in U.S. Appl. No. 14/050,166.
US Notice of Allowance, dated Apr. 8, 2014, issued in U.S. Appl. No. 14/050,166.
US Office Action, dated Jul. 29, 2014, issued in U.S. Appl. No. 14/261,344.
US Office Action, dated Jan. 14, 2014, issued in U.S. Appl. No. 14/050,182.
US Applicant Initiated Interview Summary, dated Mar. 7, 2014, issued in U.S. Appl. No. 14/050,182.
US Final Office Action, dated May 1, 2014, issued in U.S. Appl. No. 14/050,182.
US Applicant Initiated Interview Summary, dated Aug. 19, 2014, issued in U.S. Appl. No. 14/050,182.
US Office Action, dated Jun. 20, 2014, issued in U.S. Appl. No. 14/261,347.
US Office Action, dated Jul. 29, 2014, issued in U.S. Appl. No. 14/261,347.
"Activator is One of the Best Cydia iPhone Hacks | Control your iPhone with Gestures," iphone-tips-and-advice.com, [retrieved on Jul. 9, 2013 at http://www.iphone-tips-and-advice.com/activatior.html], 10 pp.
Ali-Hasan, N., Gavales, D., Peterson, A. & Raw, M., (Apr. 22-27, 2006) "Fitster: Social Fitness Information Visualizer," *in Ext. Abstr. Hum. Factors Comput. Syst., ACM Press*, 1795-1800.
Anderson, Ian et al. (Aug. 3, 2007) "Shakra: Tracking and Sharing Daily Activity Levels with Unaugmented Mobile Phones," *Mobile Networks Appl.* 12:185-199.
Bonato, P. (May/Jun. 2010) "Wearable Sensors and Systems," *IEEE Eng. In Medicine and Biology Magazine*, 29:25-36.
Buttussi, F. & Chittaro, L. (2008) "MOPET, A context-aware and user-adaptive wearable system for fitness training," *Artificial Intelligence in Medicine*, 42:153-163.
Chudnow, Alan (Dec. 3, 2012) "Basis Wristband Make Its Debut," *The Wired Self, Living in a Wired World*, published in Health [retrieved on Jul. 22, 2013 at http://thewiredself.com/health/basis-wrist-band-make-its-debut/], 3pp.

(56) References Cited

OTHER PUBLICATIONS

DesMarais, Christina (posted on Sep. 3, 2013) "Which New Activity Tracker is Best for You?" *Health and Home, Health & Fitness, Guides & Reviews*, [Retrieved on Sep. 23, 2013 at http://www.techlicious.com/guide/which-new-activity-tracker-is-right-for-you/] 4 pp.
Dobkin, B. H. & Dorsch, A. (2011) "The Promise of mHealth: Daily Activity Monitoring and Outcome Assessments by Wearable Sensors," *Neurorehabilitation and Neural Repair*, 25(9):788-98.
Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.
Fitbit User's Manual, Last Updated Oct. 22, 2009, 15 pages.
Forerunner® 10 Owner's Manual (Aug. 2012), Garmin Ltd., 10 pp.
Forerunner® 110 Owner's Manual, (2010) "GPS-Enabled Sport Watch," Garmin Ltd., 16 pp.
Forerunner® 201 personal trainer owner's manual, (Feb. 2006) Garmin Ltd., 48 pp.
Forerunner® 205/305 Owner's Manual, GPS-enabled trainer for runners, (2006-2008), Garmin Ltd., 80 pp.
Forerunner® 210 Owner's Manual, (2010) "GPS-Enabled Sport Watch," Garmin Ltd., 28 pp.
Forerunner® 301 personal trainer owner's manual, (Feb. 2006) Garmin Ltd., 66 pp.
Forerunner® 310XT Owner's Manual, Multisport GPS Training Device, (2009-2013), Garmin Ltd., 56 pp.
Forerunner® 405 Owner's Manual, (Mar. 2011) "GPS-Enabled Sport Watch With Wireless Sync," Garmin Ltd., 56 pp.
Forerunner® 405CX Owner's Manual, "GPS-Enabled Sports Watch With Wireless Sync," (Mar. 2009), Garmin Ltd., 56 pp.
Forerunner® 410 Owner's Manual, (Jul. 2012) "GPS-Enabled Sport Watch With Wireless Sync," Garmin Ltd., 52 pp.
Forerunner® 50 with ANT+Sport™ wireless technology, Owner's Manual, (Nov. 2007) Garmin Ltd., 44 pp.
Forerunner® 910XT Owner's Manual, (Jan. 2013) Garmin Ltd., 56 pp.
Gamelin, F.X., Berthoin, S. & Bosquet, L. (2006) "Validity of the Polar S810 Heart Rate Monitor to Measure R-R Intervals at Rest," *Med. Sci. Sports Exerc*. 38(5):887-893.
Garmin Swim™ Owner's Manual (Jun. 2012), 12 pp.
Gomes, N. et al. (2012) "Steptacular: An incentive mechanism for promoting wellness," *in Conf. Commun. Syst. Networks*, IEEE, 1-6.
Gupta, N. & Jilla, S. (2011) "Digital Fitness Connector: Smart Wearable System," First *International Conference on Informatics and Computational Intelligence, IEEE Computer Society*, 118-121.
Kranz, M. et al. (2013) "The mobile fitness coach: Towards individualized skill assessment using personalized mobile devices," *Pervasive Mob. Computing*, 9:203-215.
Lane, N. et al. (2010) "A survey of mobile phone sensing," *IEEE Communications Magazine*, 48:140-150.

Lark/Larkpro, User Manual, (2012) "What's in the box," *Lark Technologies*, 7 pp.
Larklife, User Manual, (2012) *Lark Technologies*, 7 pp.
Le Masurier, G. C. & Tudor-Locke, C. (2003) "Comparison of Pedometer and Accelerometer Accuracy under Controlled Conditions," *Med.& Sci. in Sports & Exerc*. 35:867-871.
Marschollek, M. et al. (Aug. 20-24, 2008) "A performance comparison of accelerometry-based step detection algorithms on a large, non-laboratory sample of healthy and mobility-impaired persons," 30th Annual International IEEE EMBS Conference, Vancouver, BC, Canada, *Eng. Med. Biol. Mag*. 1319-1322.
Milošević, M., Shrove, M. T. & Jovanov, E. (Jun. 2011) "Applications of Smartphones for Ubiquitous Health Monitoring and Wellbeing Management," *Journal of Information Technology and Applications*, 1:7-15.
Nike+ FuelBand GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
"Parts of Your Band," (Product Release Date Unknown, downloaded Jul. 22, 2013) Jawbone UP Band, 1 page.
Polar WearLink® + Coded Transmitter 31 Coded Transmitter W.I.N.D. User Manual, Polar® Listen to Your Body, *Manufactured by Polar Electro Oy*, (2010) 11 pages.
Rainmaker, (Jun. 25, 2012, updated Feb. 16, 2013) "Garmin Swim watch In-Depth Review," [retrieved on Sep. 9, 2013 at http://www.dcrainmaker.com/2012/06/garmin-swim-in-depth-review.html, 38 pp.
Schloesser, M., Schnitzer, A., Ying, H., Silex, C. & Schiek, M. (Aug. 20-24, 2008) "iSANLA: intelligent Sensor and Actuator Network for Life science Applications," i 30th Annual International IEEE EMBS Conference, Vancouver, BC, Canada, *Med. Biol. Soc*. 2369-2372.
Schneider, P.L., Crouter, S. E. & Bassett, D. R. (2004) "Pedometer Measures of Free-Living Physical Activity: Comparison of 13 Models," *Med. & Sci. in Sports & Exerc*. 36(2):331-335.
Tudor-Locke, C., Ainsworth, B.E., Thompson, R.W. & Matthews, C.E. (2002) Comparison of pedometer and accelerometer measures of free-living physical activity, *Med. Sci. Sports Exerc*. 34(12):2045-2051.
Tudor-Locke, C. et al. (Mar.-Apr. 2006) "Evaluation of Quality of Commercial Pedometers," *Can. J. Public Heal*. 97(1):S10-S15.
Ying, H., Silex, C., Schnitzer, A., Leonhardt, S. & Schiek, M. (Springer Berlin Heidelberg, 2007) "Automatic Step Detection in the Accelerometer Signal," in *Wearable Implant Body Sens. Networks* (Leonhardt, S., Falck, T. & Mahonen, P.) 13:80-85.
US Notice of Allowance, dated Feb. 5, 2015, issued in U.S. Appl. No. 14/261,347.

* cited by examiner

DELAYED GOAL CELEBRATION

CROSS REFERENCE TO RELATED APPLICATIONS

This application is a divisional of U.S. patent application Ser. No. 14/050,182, filed Oct. 9, 2013, which claims priority benefit under 35 U.S.C. §119(e) to U.S. Provisional Application No. 61/886,017, filed Oct. 2, 2013, titled "DELAYED GOAL CELEBRATION," both of which are hereby incorporated by reference in their entireties.

BACKGROUND

Recent consumer interest in personal health has led to a variety of personal health monitoring devices being offered on the market. Such devices, until recently, tended to be complicated to use and were typically designed for use with one activity, e.g., bicycle trip computers.

Recent advances in sensor, electronics, and power source miniaturization have allowed the size of personal health monitoring devices, also referred to herein as "biometric tracking" or "biometric monitoring" devices, to be offered in extremely small sizes that were previously impractical. For example, the Fitbit Ultra is a biometric monitoring device that is approximately 2" long, 0.75" wide, and 0.5" deep; it has a pixelated display, battery, sensors, wireless communications capability, power source, and interface button, as well as an integrated clip for attaching the device to a pocket or other portion of clothing, packaged within this small volume.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

In some implementations, an apparatus may be provided that has one or more biometric sensors, a display, at least one processor, and a memory. The memory, the at least one processor, the one or more biometric sensors, and the display may be communicatively connected with one another. The memory may store computer-executable instructions for controlling the at least one processor to: a) receive biometric data from the one or more biometric sensors, b) calculate at least one biometric performance measurement using the biometric data, c) determine at a first time that the at least one biometric performance measurement indicates that a first biometric performance goal has been met during a first goal achievement window, d) receive an input signal indicative of a user interaction with the apparatus, e) display a first goal celebration indicator associated with the first biometric performance goal on the display after c) and responsive to d) when the input signal is received at a second time after the first time, and f) clear the first goal celebration indicator after e).

In some implementations of the apparatus, the input signal may be produced by activation of a button of the apparatus, selection of a touch-screen control of the apparatus, detection of biometric data indicative of a wearer of the apparatus bringing their forearm into a watch-viewing position, or detection of biometric data indicative of one or more successive taps on the apparatus (or combinations thereof).

In some implementations, the memory may further store computer-executable instructions for controlling the at least one processor to: g) determine at a third time that the at least one biometric performance measurement indicates that a second biometric performance goal different from the first biometric performance goal has been met during a second goal achievement window, h) display a second goal celebration indicator associated with the second biometric performance goal on the display after g) and responsive to d) when the second time is after the third time, and i) clear the second goal celebration indicator after h).

In some implementations, the second biometric performance goal may include a plurality of different biometric performance goals and the second biometric performance goal may be met by meeting any one of the biometric performance goals in the plurality of different biometric performance goals.

In some implementations, the first goal celebration may be selected randomly from a pool of available goal celebrations.

In some implementations, the apparatus may further include a tactile indicator, and the memory may store further computer-executable instructions for controlling the at least one processor to activate the tactile indicator responsive to c) and independently of d).

In some implementations, the apparatus may further include a tactile indicator and the memory may store further computer-executable instructions for controlling the at least one processor to: g) determine whether the apparatus is in a sleep-monitoring mode, and h) activate the tactile indicator responsive to c) and independently of d) when the at least one processor determines in g) that the apparatus is not in a sleep monitoring mode.

In some implementations, the apparatus may further include a tactile indicator, and the memory may store further computer-executable instructions for controlling the at least one processor to: g) determine that the biometric data during at least a first period of time indicates a first activity state associated with the first biometric performance goal, and h) activate the tactile indicator independently of d) and when c) occurs during the first period of time.

In some implementations of the apparatus, the memory may store further computer-executable instructions for controlling the at least one processor to g) reset progress towards the first biometric performance goal after the first goal achievement window has elapsed, thereby initiating an additional first goal achievement window subsequent to the first goal achievement window.

In some such implementations, the memory may store further computer-executable instructions for controlling the at least one processor to determine that g) has been performed after c) without the performance of e) in between c) and g) and, responsive to d) occurring during the additional first goal achievement window, perform e).

In some implementations, the first goal achievement window may have a duration such as 1 hour, 8 hours, 1 day, 5 days, 1 week, or 1 month. In some implementations, the first goal achievement window may be a 24-hour period starting or ending at midnight, a 7-day period starting or ending on a weekend, or a 1 month period starting on the first day of a month.

In some implementations, the at least one biometric performance measurement may be calculated by incrementing the at least one biometric performance measurement, at least in part, each time the biometric data exceeds a threshold. In such implementations, the memory may store further computer-executable instructions for controlling the at least one processor to increase the threshold when the at least one biometric performance measurement indicates that a substantial portion of the first biometric performance goal has been met.

In some such implementations, the substantial portion of the first biometric performance goal may be approximately 90% (or higher) of the first biometric performance goal. In some implementations, the threshold may be increased by more than 10%.

In some implementations, a method may be provided. The method may include performing the steps of a) receiving, by a controller having one or more processors, biometric data from one or more biometric sensors; b) calculating, using the controller, at least one biometric performance measurement using the biometric data; c) determining, by the controller, at a first time that the at least one biometric performance measurement indicates that a first biometric performance goal has been met during a first goal achievement window; d) receiving, by the controller, an input signal indicative of a user interaction with an apparatus that includes the controller, the one or more biometric sensors, and a display; e) causing the controller to display a first goal celebration indicator associated with the first biometric performance goal on the display after c) and responsive to d) when the input signal is received at a second time after the first time; and f) clearing the first goal celebration indicator after e).

In some implementations of the method, the input signal may be produced by activation of a button of the apparatus, selection of a touch-screen control of the apparatus, detection of biometric data indicative of a wearer of the apparatus bringing their forearm into a watch-viewing position, detection of biometric data indicative of one or more successive, rapid taps on the apparatus, or combinations thereof.

In some implementations of the method, the method may also include g) determining at a third time that the at least one biometric performance measurement indicates that a second biometric performance goal different from the first biometric performance goal has been met during a second goal achievement window, h) displaying a second goal celebration indicator associated with the second biometric performance goal on the display after g) and responsive to d) when the second time is after the third time, and i) clearing the second goal celebration indicator after h).

In some such implementations of the method, the second biometric performance goal includes a plurality of different biometric performance goals and the second biometric performance goal may be met by meeting any one of the biometric performance goals in the plurality of different biometric performance goals.

In some implementations of the method, the first goal celebration may be selected randomly from a pool of available goal celebrations.

In some implementations of the method, the apparatus may further include a tactile indicator, and the method may further include g) activating the tactile indicator responsive to c) and independently of d).

In some implementations of the method, the apparatus may further include a tactile indicator, and the method may further include g) determining whether the apparatus is in a sleep-monitoring mode, and h) activating the tactile indicator responsive to c) and independently of d) when it is determined in g) that the apparatus is not in a sleep monitoring mode.

In some implementations of the method, the apparatus may further include a tactile indicator, and the method may further include g) determining, by the controller, that the biometric data during at least a first period of time indicates a first activity state associated with the first biometric performance goal, and h) activating the tactile indicator independently of d) and when c) occurs during the first period of time.

In some implementations of the method, the method may further include g) resetting progress towards the first biometric performance goal after the first goal achievement window has elapsed and thereby initiating an additional first goal achievement window subsequent to the first goal achievement window. In some such implementations of the method, the method may further include h) determining that g) has been performed after c) without the performance of e) in between c) and g). The method of such implementations may also include i) responsive to d) occurring during the additional first goal achievement window, performing e).

In some implementations of the method, the first goal achievement window may have a 1 hour, 8 hours, 1 day, 5 days, 1 week, or 1 month duration.

In some implementations of the method, the first goal achievement window may be a 24-hour period starting or ending at midnight, a 7-day period starting or ending on a weekend, or a 1 month period starting on the first day of a month.

In some implementations of the method, b) may be performed by incrementing the at least one biometric performance measurement, at least in part, each time the biometric data exceeds a threshold, and the method may further include g) increasing the threshold when the at least one biometric performance measurement indicates that a substantial portion of the first biometric performance goal has been met.

In some implementations of the method, the substantial portion of the first biometric performance goal may be approximately 90% of the first biometric performance goal or higher. In some implementations of the method, the threshold may be increased by more than 10%.

In some implementations, an apparatus may be provided that includes a housing, one or more biometric sensors, at least one processor, and a memory. The memory, the at least one processor, and the one or more biometric sensors may be communicatively connected with one another. The memory may store computer-executable instructions for controlling the at least one processor to: a) receive biometric data from the one or more biometric sensors, b) calculate at least one biometric performance measurement using the biometric data, c) determine at a first time that the at least one biometric performance measurement indicates that a first biometric performance goal has been met during a first goal achievement window, d) receive an input signal indicative of a user interaction with an item selected from the group consisting of: the apparatus and a remote device in communication with the apparatus, and e) generate a first output signal associated with the first biometric performance goal after c) and responsive to d) when the input signal is received at a second time after the first time.

In some implementations of the apparatus, the input signal may be produced through activation of a button of the apparatus, selection of a touch-screen control of the apparatus, detection of biometric data indicative of a wearer of the apparatus bringing their forearm into a watch-viewing position, detection of biometric data indicative of one or more successive taps on the housing, receipt of a wireless signal from the remote device, or combinations thereof.

In some implementations of the apparatus, the memory may store further computer-executable instructions for controlling the at least one processor to: f) determine at a third time that the at least one biometric performance measurement indicates that a second biometric performance goal different from the first biometric performance goal has been met during a second goal achievement window, and g) generate a second output signal associated with the second biometric performance goal after f) and responsive to d) when the second time is after the third time.

In some such implementations of the apparatus, the second biometric performance goal may include a plurality of different biometric performance goals and the second biometric performance goal may be met by meeting any one of the biometric performance goals in the plurality of different biometric performance goals.

In some implementations, the memory may store further computer-executable instructions for controlling the at least one processor to: f) generate a first notification signal responsive to c) and independently of d).

In some implementations of the apparatus, the first notification signal may be a signal that causes the display of a notification indicator on a display of the apparatus, the activation of a haptic device of the apparatus, the emission of an auditory notification indicator from an audio device of the apparatus, or combinations thereof.

In some implementations of the apparatus, the first notification signal may be a wireless signal formatted for receipt by the remote device. In some such implementations, the remote device may be a smartphone.

In some implementations of the apparatus, the first output signal may be a wireless signal formatted for receipt by the remote device. Again, in some such implementations, the remote device may be a smartphone.

In some implementations, a method may be provided. The method may include a) receiving biometric data from one or more biometric sensors; b) calculating at least one biometric performance measurement using the biometric data; c) determining, at a first time, that the at least one biometric performance measurement indicates that a first biometric performance goal has been met during a first goal achievement window; d) receiving, by the controller, an input signal indicative of a user interaction with an item selected from the group consisting of: a biometric monitoring device and a mobile communications device; and e) generating a first output signal associated with meeting the first biometric performance goal after c) and responsive to d) when the input signal is received at a second time after the first time.

In some implementations of the method, the input signal may be produced through: activation of a button of the biometric monitoring device, selection of a touch-screen control of the biometric monitoring device, detection of biometric data indicative of a wearer of the biometric monitoring device bringing their forearm into a watch-viewing position, detection of biometric data indicative of one or more successive taps on the biometric monitoring device, receipt of a wireless signal from the mobile communications device, or combinations thereof.

In some implementations of the method, the method may further include f) determining at a third time that the at least one biometric performance measurement indicates that a second biometric performance goal different from the first biometric performance goal has been met during a second goal achievement window, and g) causing the controller to generate a second output signal associated with meeting the second biometric performance goal after g) and responsive to d) when the second time is after the third time.

In some implementations of the method, the second biometric performance goal may include a plurality of different biometric performance goals and the second biometric performance goal may be met by meeting any one of the biometric performance goals in the plurality of different biometric performance goals.

In some implementations of the method, the method may further include f) causing the controller to generate a first notification signal responsive to c) and independently of d).

In some implementations of the method, the first notification signal may cause the display of a goal celebration indicator on a display of the biometric monitoring device, the activation of a haptic device of the biometric monitoring device, the emission of an auditory goal celebration indicator from an audio device of the biometric monitoring device, or combinations thereof.

In some implementations of the method the first notification signal may be a wireless signal formatted for receipt by the mobile communications device. In some such implementations, the mobile communications device may be a smartphone.

In some implementations of the method the first output signal may be a wireless signal formatted for receipt by the mobile communications device. In some such implementations, the mobile communications device may be a smartphone.

In some implementations, a system may be provided that includes a biometric monitoring device and a mobile communications device separate from the biometric monitoring device. The biometric monitoring device may have one or more biometric sensors, at least one processor, a communications interface, and a memory. The memory, the at least one processor, the communications interface, and the one or more biometric sensors may be communicatively connected with one another. The memory may store computer-executable instructions for controlling the at least one processor to: a) receive biometric data from the one or more biometric sensors, b) calculate at least one biometric performance measurement using the biometric data, c) determine at a first time that the at least one biometric performance measurement indicates that a first biometric performance goal has been met during a first goal achievement window, and d) transmit a first output signal associated with the first biometric performance goal via the communications interface after c). The mobile communications device may have: at least one mobile communications device processor, a mobile communications device memory, and a mobile communications device communications interface. The at least one mobile communications device processor, the mobile communications device memory, and the mobile communications device communications interface may be communicatively connected with one another. The mobile communications device memory may store computer-executable instructions for controlling the at least one mobile communications device processor to: e) receive the first output signal transmitted from the biometric monitoring device in d), f) receive a first input signal, and g) responsive to f) and after e), cause the mobile communications device to produce a goal celebration indicator associated with meeting the first biometric performance goal.

In some such implementations, the first input signal may be generated by the mobile communications device responsive to the at least one mobile communications device processor detecting the powering on the mobile communications device from an off state, the transitioning on the mobile communications device from a standby state to an on state, the activation of a software program associated with the biometric monitoring device, the push of a button on the mobile communications device, the selection of a touch-screen control on the mobile communications device, the receipt of a communication from the biometric monitoring device via the mobile device communications interface, or combinations thereof.

In some implementations of the system, the goal celebration indicator may be a display of graphical content on a display of the mobile communications device, tactile feedback provided by a haptic mechanism of the mobile communications device, audio output provided by an audio device of the mobile communications device, or combinations thereof.

In some implementations of the system, the mobile communications device memory stores further computer-executable instructions for controlling the at least one mobile communications device processor to h) responsive to e) and independent of f), cause the mobile communications device to provide a first notification indicator.

In some such implementations of the system, the first notification indicator may be a display of graphical content on a display of the mobile communications device, tactile feedback provided by a haptic mechanism of the mobile communications device, audio output provided by an audio device of the mobile communications device, or combinations thereof.

In some implementations, a system may be provided that includes a biometric monitoring device and at least one remote device separate from the biometric monitoring device, e.g., a smartphone, a server, a smartphone and a server, etc. The biometric monitoring device may have one or more biometric sensors, at least one processor, a communications interface, and a memory. The memory, the at least one processor, the communications interface, and the one or more biometric sensors may be communicatively connected with one another. The memory may store computer-executable instructions for controlling the at least one processor to: a) receive biometric data from the one or more biometric sensors. The at least one remote device may have at least one remote device processor, a remote device communications interface, and a remote device memory. The remote device memory, the at least one remote device processor, and the remote device communications interface of the at least one remote device may be communicatively connected with one another. The memory and the at least one remote device memory may store, in aggregate, computer-executable instructions for controlling the system to: b) calculate at least one biometric performance measurement using the biometric data, c) determine whether a user-specified biometric performance goal has been met based on the at least one biometric performance measurement, d) provide, responsive to c), a notification indicator that the user-specified biometric performance goal has been met, e) receive an input signal indicating a user interaction with an item selected from the group consisting of the biometric monitoring device and the at least one remote device, and f) provide, responsive to e) and after c), a goal celebration indicator such as a graphical display of visual elements associated with meeting the biometric performance goal, audible sounds associated with meeting the biometric performance goal, tactile feedback associated with meeting the biometric performance goal, or combinations thereof.

These and other implementations are described in further detail with reference to the Figures and the detailed description below.

BRIEF DESCRIPTION OF THE DRAWINGS

The various implementations disclosed herein are illustrated by way of example, and not by way of limitation, in the figures of the accompanying drawings, in which like reference numerals may refer to similar elements.

DETAILED DESCRIPTION

Figure 1:
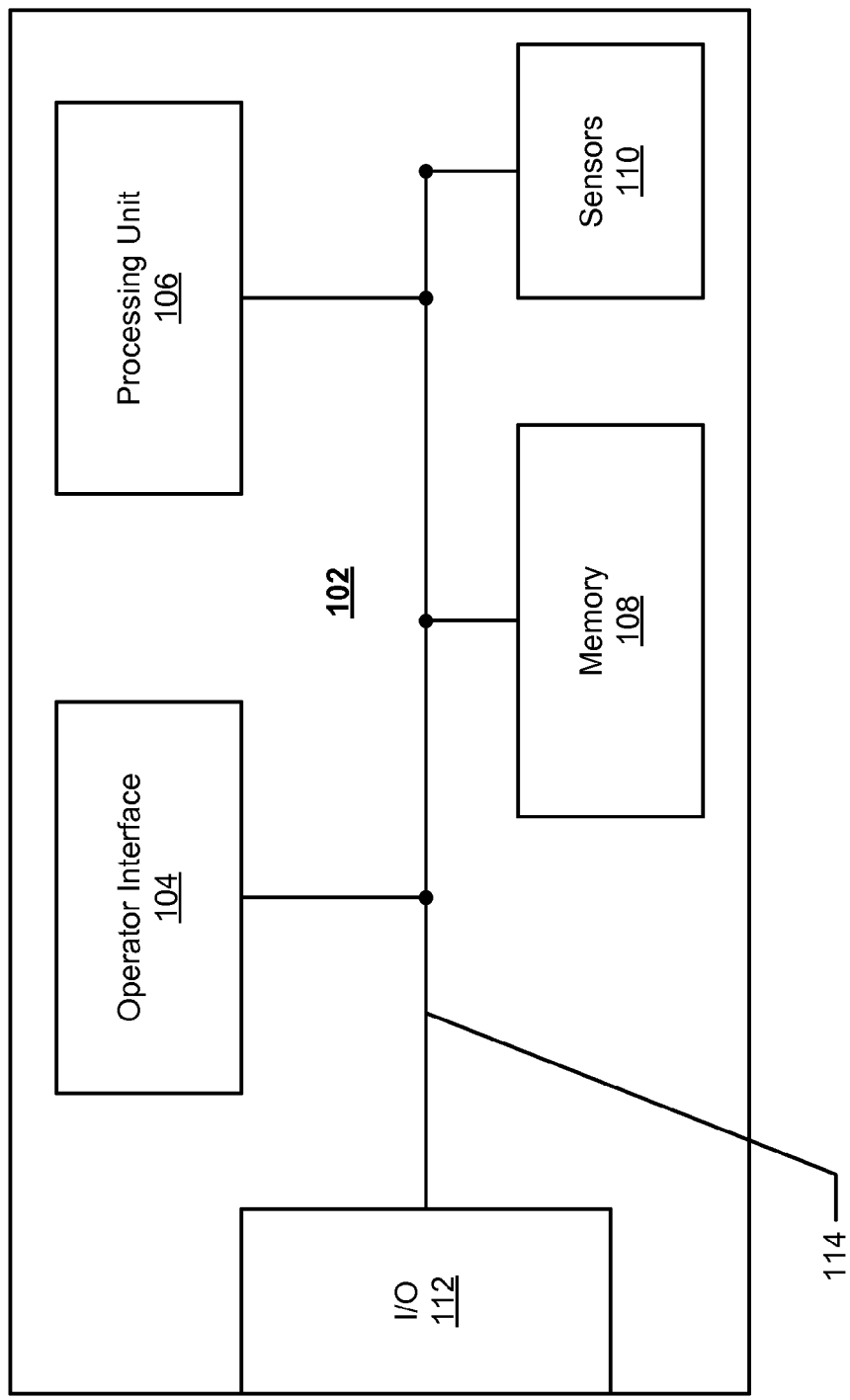
FIG. 1 depicts a generalized schematic of an example computing device that may be used to implement a portable biometric monitoring device or other device with which the various operations described herein may be executed.
Figure 2A:
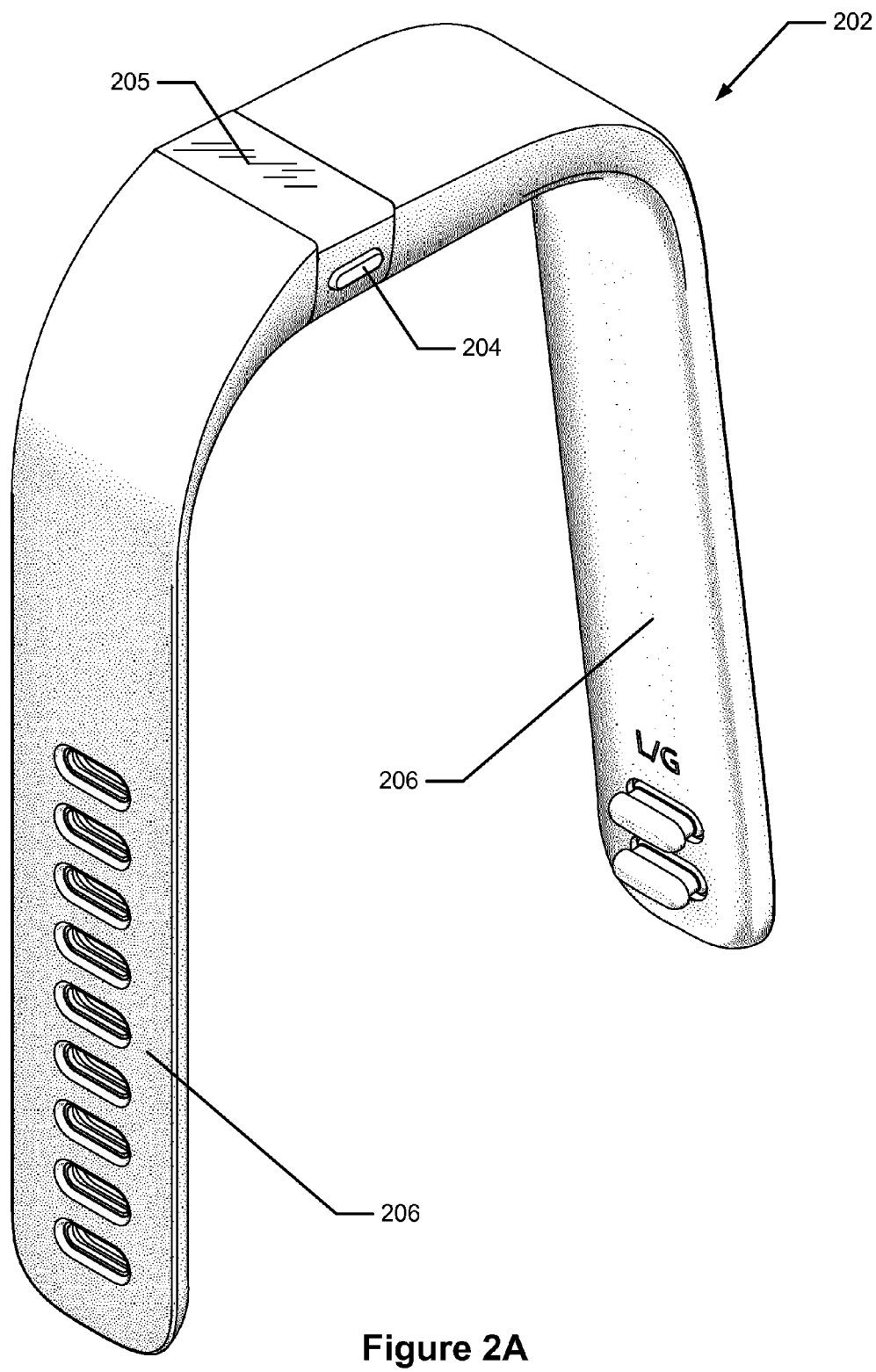
FIGS. 2A through 2G depict various views of an example biometric monitoring device.
Figure 2B:
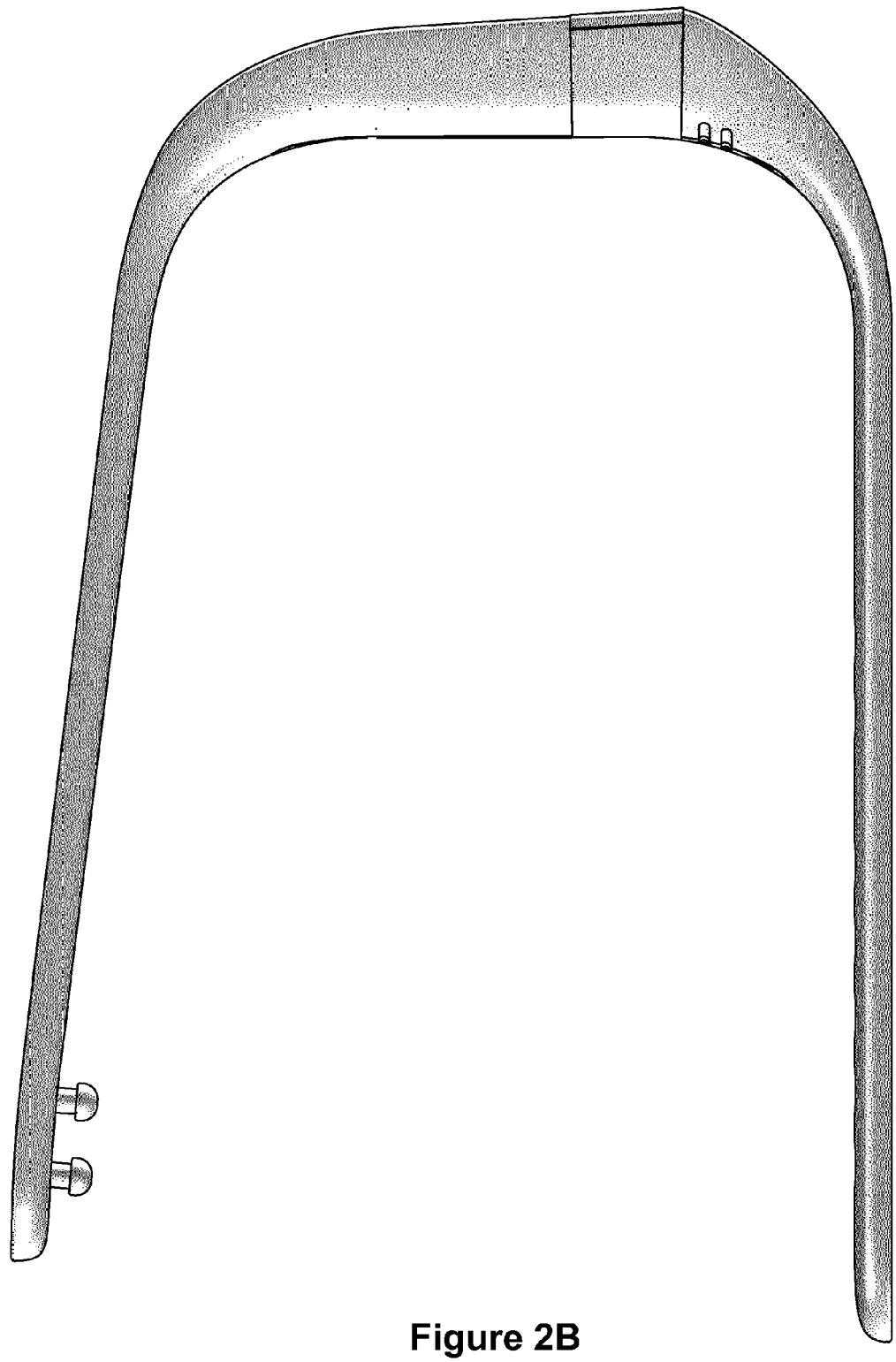
Figure 2C:
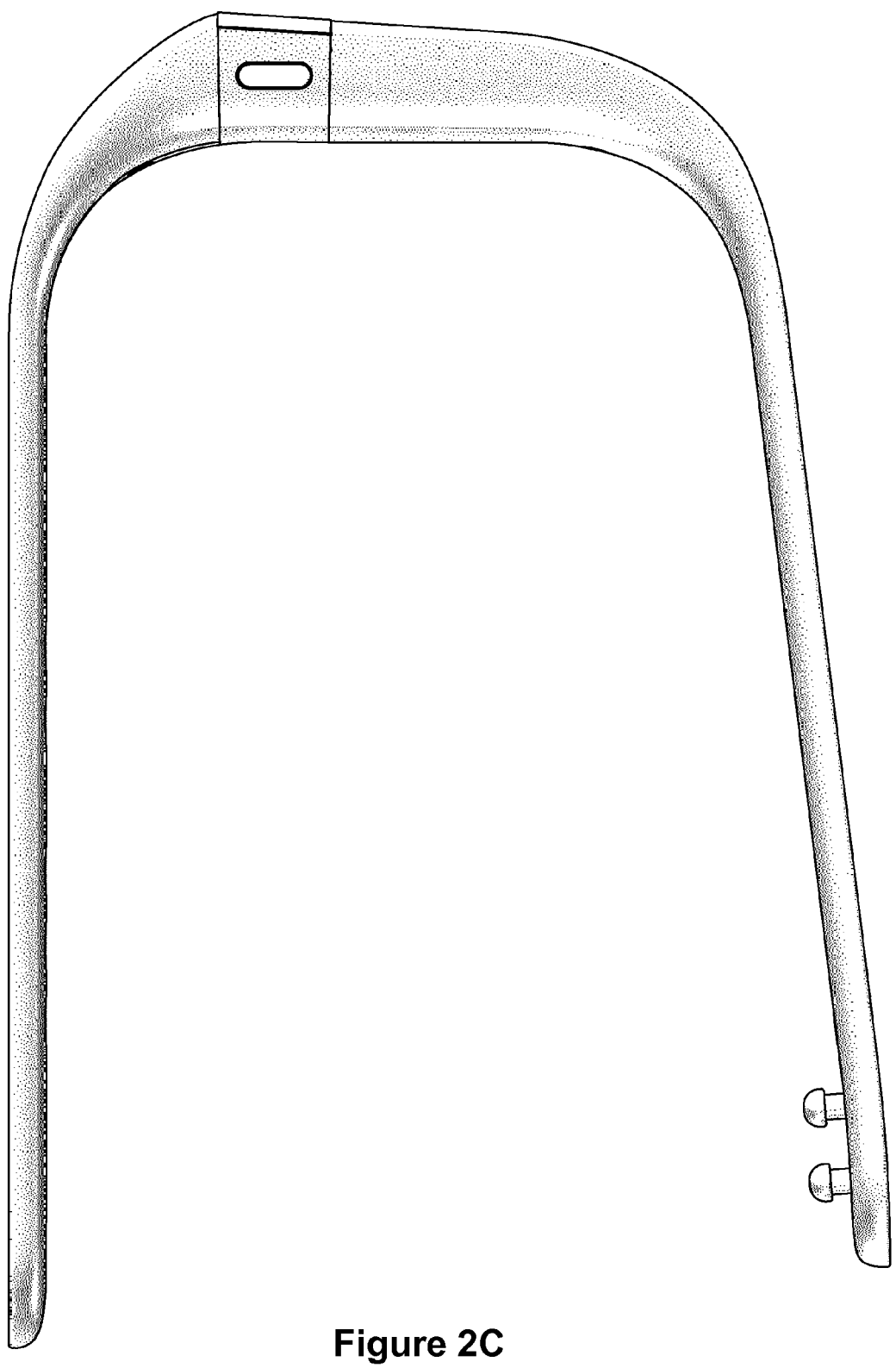
Figure 2D:
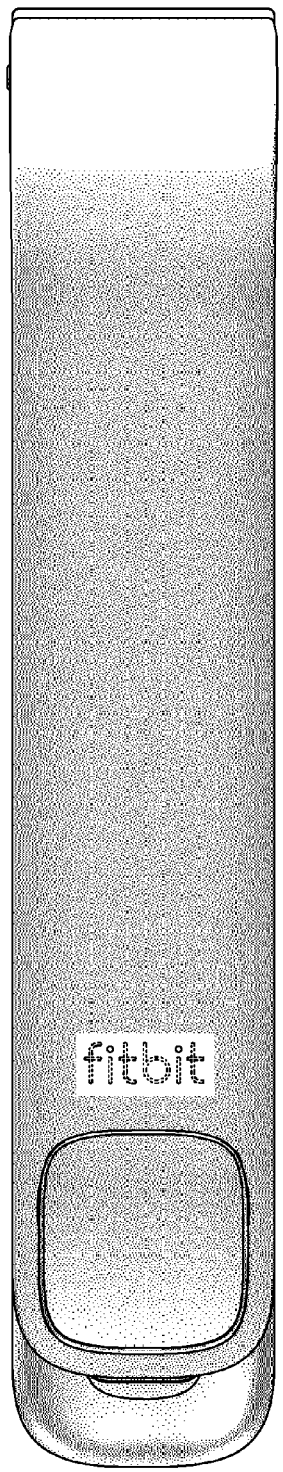
Figure 2E:
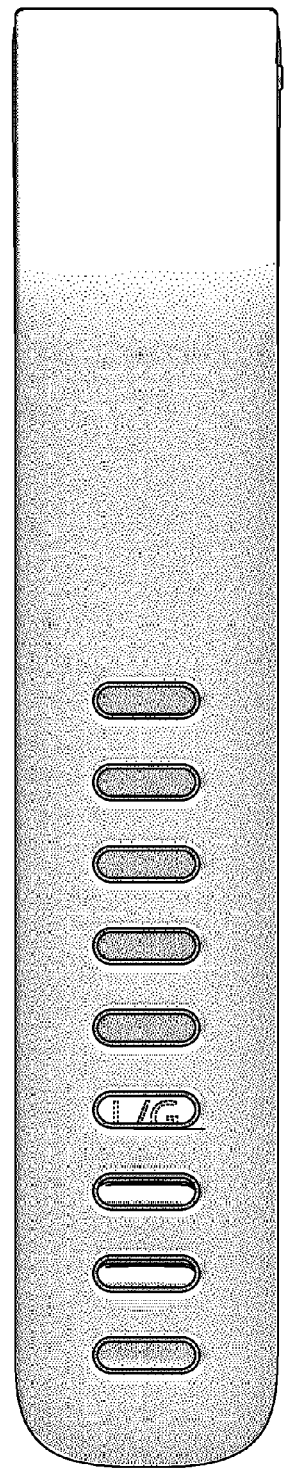
Figure 2F:
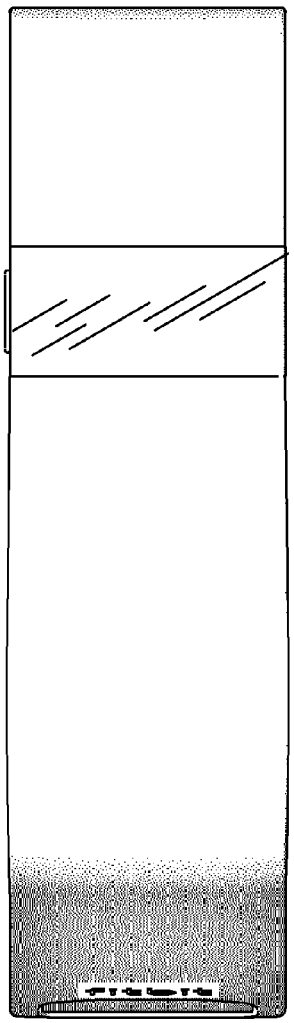
Figure 2G:
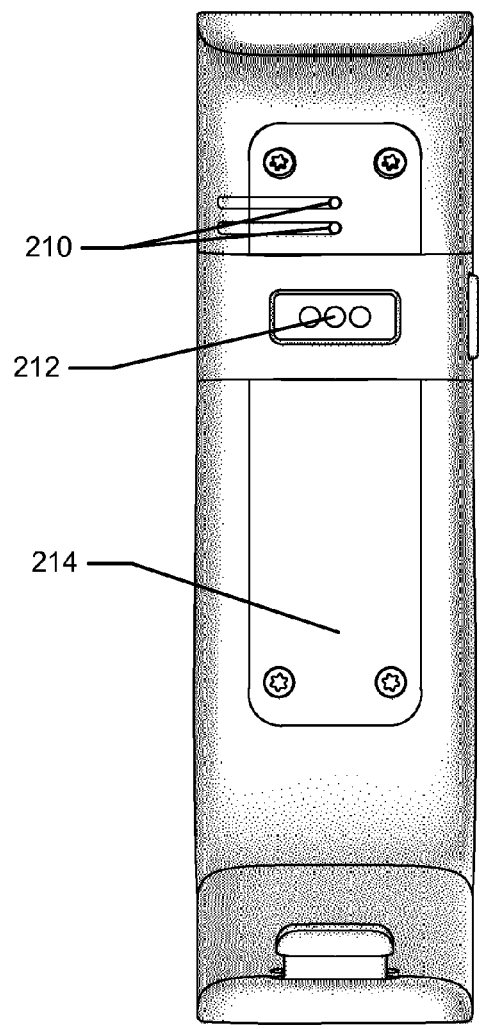

The present disclosure relates to wearable biometric monitoring devices (also referred to herein as "biometric tracking devices" or simply as "devices") such as those, for example, illustrated schematically in FIG. 1. In some implementations, a biometric monitoring device may be designed such that it may be inserted into, and removed from, a plurality of compatible cases/housings/holders, e.g., a wristband that may be worn on a person's forearm or a belt clip case that may be attached to a person's clothing. Generally speaking, a biometric monitoring device or biometric tracking device combined with a case or some other means allowing it to be worn or easily carried by a person may be referred to herein as a "biometric monitoring system" or "biometric tracking system."

As used herein, the term "wristband" may refer to a band that is designed to fully or partially encircle a person's forearm near the wrist joint. The band may be continuous, e.g., without any breaks (it may stretch to fit over a person's hand or have an expanding portion similar to a dress watchband), or may be discontinuous, e.g., having a clasp or other connection allowing the band to be closed similar to a watchband or may be simply open, e.g., having a C-shape that clasps the wearer's wrist.

FIG. 1 depicts a generalized schematic of an example portable biometric monitoring device, also simply referred to herein as "biometric monitoring device," or other device with which the various operations described herein may be executed. The portable biometric monitoring device 102 may include a processing unit 106 having one or more processors, a memory 108, an operator interface 104, one or more biometric sensors 110, and input/output 112. The processing unit 106, the memory 108, the operator interface 104, the one or more biometric sensors 110, and the input/output interface 112 may be communicatively connected via communications path(s) 114 (it is to be understood that some of these components may also be connected with one another indirectly).

The portable biometric monitoring device may collect one or more types of biometric data, e.g., data pertaining to physical characteristics of the human body (such as heartbeat, perspiration levels, etc.) and/or data relating to the physical interaction of that body with the environment (such as accelerometer readings, gyroscope readings, etc.), from the one or more biometric sensors 110 and/or external devices (such as an external heart rate monitor, e.g., a chest-strap heart rate monitor) and may then store such information for later use, e.g., for communication to another device via the I/O interface 112, e.g., a smartphone or to a server over a wide-area network such as the Internet. The processing unit 106 may also perform an analysis on the stored data and may initiate various actions depending on the analysis. For example, the processing unit 106 may determine that the data stored in the memory 108 indicates that a goal threshold has been reached and may then display content on a display of the portable biometric monitoring device celebrating the achievement of the goal. The display may be part of the operator interface 104 (as may be a button or other control, not pictured, that may be used to control a functional aspect of the portable biometric monitoring device).

In general, biometric monitoring devices may incorporate one or more types of user interfaces including but not limited to visual, auditory, touch/vibration, or combinations thereof. The biometric monitoring device may, for example, display information relating to one or more of the data types available and/or being tracked by the biometric monitoring device through, for example, a graphical display or through the intensity and/or color of one or more LEDs. The user interface may also be used to display data from other devices or internet sources. The device may also provide haptic feedback through, for instance, the vibration of a motor or a change in texture or shape of the device. In some implementations, the biometric sensors themselves may be used as part of the user interface, e.g., accelerometer sensors may be used to detect when a person taps the housing of the biometric monitoring unit with a finger or other object and may then interpret such data as a user input for the purposes of controlling the biometric monitoring device. For example, double-tapping the housing of the biometric monitoring device may be recognized by the biometric monitoring device as a user input that will cause the display of the biometric monitoring device to turn on from an off state or that will cause the biometric monitoring device to transition between different monitoring states, e.g., from a state where the biometric monitoring device may interpret data according to rules established for an "active" person to a state where the biometric monitoring device may interpret data according to rules established for a "sleeping" person.

In another example, while the user is wearing the biometric monitoring device 102, the biometric monitoring device 102 may calculate and store a user's step count while the user is wearing the biometric monitoring device 102 and then subsequently transmit data representative of step count to the user's account on a web service like www.Fitbit.com, to a mobile computational device, e.g., a phone, paired with the portable biometric monitoring unit, and/or to a standalone computer where the data may be stored, processed, and visualized by the user. Such transmission may be carried out via communications through I/O interface 112. Indeed, the device may measure, calculate, or use a plurality of other physiological metrics in addition to, or in place of, the user's step count. These include, but are not limited to, caloric energy expenditure, floors climbed or descended, heart rate, heart rate variability, heart rate recovery, location and/or heading (e.g., through GPS), elevation, ambulatory speed and/or distance traveled, swimming lap count, bicycle distance and/or speed, blood pressure, blood glucose, skin conduction, skin and/or body temperature, electromyography data, electroencephalographic data, weight, body fat, and respiration rate. Some of this data may be provided to the biometric monitoring device from an external source, e.g., the user may input their height, weight, and stride in a user profile on a fitness-tracking website and such information may then be communicated to the biometric monitoring device via the I/O interface 112 and used to evaluate, in tandem with data measured by the biometric sensors 110, the distance traveled or calories burned of the user. The device may also measure or calculate metrics related to the environment around the user such as barometric pressure, weather conditions, light exposure, noise exposure, and magnetic field.

As mentioned previously, collected biometric data from the biometric monitoring device may be communicated to external devices through the communications or I/O interface 112. The I/O or communications interface may include wireless communication functionality so that when the biometric monitoring device comes within range of a wireless base station or access point, the stored data automatically uploads to an Internet-viewable source such as a website, e.g., www.Fitbit.com. The wireless communications functionality may be provided using one or more communications technologies known in the art, e.g., Bluetooth, RFID, Near-Field Communications (NFC), Zigbee, Ant, optical data transmission, etc. The biometric monitoring device may also contain wired communication capability, e.g., USB.

Other implementations regarding the use of short range wireless communication are described in U.S. patent application Ser. No. 13/785,904, titled "Near Field Communication System, and Method of Operating Same" filed Mar. 5th 2013 which is hereby incorporated herein by reference in its entirety.

It is to be understood that FIG. 1 illustrates a generalized implementation of a biometric monitoring device 102 that may be used to implement a portable biometric monitoring device or other device in which the various operations described herein may be executed. It is to be understood that in some implementations, the functionality represented in FIG. 1 may be provided in a distributed manner between, for example, an external sensor device and communication device, e.g., a chest-strap heart rate sensor that may communicate with a biometric monitoring device.

Moreover, it is to be understood that in addition to storing program code for execution by the processing unit to effect the various methods and techniques of the implementations described herein, the memory 108 may also store configuration data or other information used during the execution of various programs or instruction sets or used to configure the biometric monitoring device. The memory 108 may also store biometric data collected by the biometric monitoring device. It is to be further understood that the processing unit may be implemented by a general or special purpose processor (or set of processing cores) and thus may execute sequences of programmed instructions to effectuate the various operations associated with sensor device syncing, as well as interaction with a user, system operator or other system components. In some implementations, the processing unit may be an application-specific integrated circuit.

Though not shown, numerous other functional blocks may be provided as part of the biometric monitoring device 102 according to other functions it may be required to perform, e.g., environmental sensing functionality, etc. Other functional blocks may provide wireless telephony operations with respect to a smartphone and/or wireless network access to a mobile computing device, e.g., a smartphone, tablet computer, laptop computer, etc. The functional blocks of the biometric monitoring device 102 are depicted as being coupled by the communication path 114 which may include any number of shared or dedicated buses or signaling links. More generally, however, the functional blocks shown may be interconnected using a variety of different architectures and may be implemented using a variety of different underlying technologies and architectures. With regard to the memory architecture, for example, multiple different classes of storage may be provided within the memory 108 to store different classes of data. For example, the memory 108 may include non-volatile storage media such as fixed or removable magnetic, optical, or semiconductor-based media to store executable code and related data and/or volatile storage media such as static or dynamic RAM to store more transient information and other variable data.

The various methods and techniques disclosed herein may be implemented through execution of one or more a sequences of instructions, e.g., software programs, by the processing unit 106 or by a custom-built hardware ASIC (application-specific integrated circuit) or programmed into a programmable hardware device such as an FPGA (field-programmable gate array), or any combination thereof within or external to the processing unit 106.

Further implementations of portable biometric monitoring devices can be found in U.S. patent application Ser. No. 13/156,304, titled "Portable Biometric Monitoring Devices and Methods of Operating Same" filed Jun. 8, 2011, which is hereby incorporated herein by reference in its entirety.

In some implementations, the biometric monitoring device may include computer-executable instructions for controlling one or more processors of the biometric monitoring device to obtain biometric data from one or more biometric sensors. The instructions may also control the one or more processors to receive a request, e.g., an input from a button or touch interface on the biometric monitoring device, a particular pattern of biometric sensor data (e.g., a double-tap reading), etc., to display an aspect of the obtained biometric data on a display of the biometric monitoring device. The aspect may be a numerical quantity, a graphic, or simply an indicator (a goal progress indicator, for example). In some implementations, the display may be an illuminable display so as to be visible when displaying data but otherwise invisible to a casual observer. The instructions may also cause the one or more processors to cause the display to turn on from an off state in order to display the aspect of the biometric data. The instructions may also cause the display to turn off from an on state after a predefined time period elapses without any user interaction with the biometric monitoring device; this may assist in conserving power.

Due to the small size of many biometric monitoring devices, many biometric monitoring devices may have limited space to accommodate various user interface components. For example, Fitbit makes a variety of extremely compact biometric tracking units that each incorporate a biometric sensor suite, a battery, a display of some sort, a charging interface, and one or more wireless communications interfaces. In some such examples, the biometric tracking units also incorporate a vibramotor and/or a button. These components may be housed, for example, within housings measuring approximately 2" long, 0.75" wide, and 0.5" thick (Fitbit Ultra™); approximately 1.9" in length, 0.75" wide, and 0.375" thick (Fitbit One approximately 1.4" long, 1.1" wide, and 0.375" thick (Fitbit Zip™); and approximately 1.3" in length, 0.5" wide, and 0.25" thick (Fitbit Flex™). Of course, housings of other sizes may be used in other implementations of biometric monitoring devices; the above list is merely intended to illustrate the small size of many such biometric monitoring devices.

FIGS. 2A through 2G depict various views of an example biometric monitoring device. The biometric monitoring device 202 of FIGS. 2A through 2G is similar to a Fitbit Force™ biometric monitoring device. The biometric monitoring device 202 may be designed such that it may be worn by a person, e.g., as a wristband (similar to a wristwatch) or as a belt-clip module (not shown, although the Fitbit One is an example of such a product). The biometric monitoring device 202 may have a display 205 that is configured to present biometric performance measurements to a wearer of the biometric monitoring device. A button 204 (or other mechanism capable of identifying a deliberate user input) may, when activated, provide an input signal to a processor or processors of the biometric monitoring device 202 that may, for example, cause the content displayed on the display 205 to change. The display 205 may be small, e.g., on the order of less than 1" square.

The biometric monitoring device 202 may include one or more biometric sensors, e.g., triaxial accelerometers (not shown, but located inside housing 214) and a barometric sensor (also not shown, although pressure ports 210 lead to a barometric sensor within the housing 214).

Biometric monitoring devices such as the implementations discussed herein may be configured make various biometric performance measurements, e.g., steps taken, distance walked and/or run, flights of stairs climbed, approximate calories burned, etc. Such biometric performance measurements may be made, at least in part, based on biometric data collected by the biometric sensors of the biometric monitoring device. For example, biometric acceleration data may be analyzed at regular intervals, e.g., every second, to determine if the biometric monitoring device (and, presumably, the wearer of the biometric monitoring device) is experiencing an acceleration environment consistent with walking or running. If so, then each biometric data segment that may be interpreted as representing a step may cause a related biometric performance measurement of "steps taken" to be incremented by one. For example, walking may produce a fairly regular vertical acceleration spike every time a person takes a step—each such spike may cause the biometric performance measurement of "steps taken" to be incremented by one (or, if desired, every two such spikes may cause an increment to occur—this may be used when steps are used to indicate strides rather than discrete steps). In another example, distance traveled may be determined by incrementing a distance traveled biometric performance measurement by a distance associated with each step that is determined—the distance may be a default distance based on the average person's stride, or may be specified by the user to more precisely tailor the distance traveled biometric performance measurement.

In a further example, the biometric sensors may include a barometric sensor that may produce biometric data that indicates the altitude of the biometric monitoring device. Each change in altitude commensurate with the altitude change experienced climbing a standard flight of stairs may cause a biometric performance measurement indicating the number of stair flights climbed to be incremented by one flight of stairs. In some implementations, the rate of altitude change may also be accounted for—if the altitude change is too rapid, i.e., so rapid that it exceeds stair-climbing rates achievable by humans, then the altitude change may not cause the biometric performance measurement to change. Similarly, if an altitude change is detected without any corresponding acceleration data indicating that the wearer of the biometric monitoring device is walking or running, this may be interpreted as indicating that the wearer may be riding an escalator. In such cases, the biometric performance measurement may not be incremented to account for the altitude change since it is not indicative of an aspect of the wearer's biometric performance.

In many implementations, the biometric performance measurements monitored by a biometric monitoring device may accumulate over a common, fixed period of time, e.g., daily. In other implementations, however, one or more of the biometric performance measurements may be accumulated over different periods of time, e.g., some biometric performance measurements may be accumulated over the course of a day, whereas others may be accumulated over the course of an hour, a week, a month, etc.

The biometric monitoring devices described herein may be configured to track biometric performance goals. Biometric performance goals are defined as targets for biometric performance measurements that must be met within one or more defined time periods, referred to herein as goal achievement windows. In many implementations, the goal achievement window for a biometric performance goal may be coextensive with the accumulation period of the biometric performance measurement upon which the biometric performance goal is based, e.g., if the "steps taken" biometric performance measurement is accumulated over the course of a day and then re-set at midnight in preparation for the next day, a biometric performance goal based on the "steps taken" biometric performance measurement may need to be achieved within a goal achievement window sharing the same 24-hour period.

Biometric performance goals, as used herein, may refer to biometric performance goals that are either generic (which may be referred to as "achievements") or that are user-specified (which may be referred to as "user-specified biometric performance goals"). Achievements are biometric performance goals that are generally automatically set by a third party, e.g., a provider of a biometric monitoring device, absent any request by a user of the biometric monitoring device. In contrast, user-specified biometric performance goals are in response to a request by a user—the request may be a specific request by a user, e.g., "set a goal of 15,000 steps per day," or may be an implicit request, e.g., the user may use a fitness website or application to plan a weight-loss regimen and may request that the website or application generate goals that are tailored to their desired regimen—while the user may not specifically set any of the specific biometric performance goals in such a scenario, those biometric performance goals may still be established in response to a user request and would thus qualify as user-specified biometric performance goals. The techniques described herein may be applied to either type of biometric performance goal. However, given the personal investment that a person may have in a user-specified biometric performance goal, it is likely that the techniques outlined herein may be of particular benefit in the context of user-specified biometric performance goals.

The goal achievement window does not necessarily need to be coextensive with the accumulation period of the biometric performance measurement upon which it is based. In some implementations, the goal achievement window may not be coextensive with the accumulation period. For example, a biometric monitoring device may monitor a person's progress towards a biometric performance goal of "Take 1000 steps in less than 5 minutes." In this case, the goal achievement window is 5 minutes in length and is not tied to any predetermined start or finish time. For example, the goal achievement window may be a floating goal achievement window that is constantly being updated as time goes on and the goal is not met.

In some implementations, the accumulation of a biometric performance measurement may be reset, e.g., at the end of the accumulation period, but the progress towards an associated biometric performance goal may be retained if the goal achievement window for the biometric performance goal straddles between two or more such accumulation periods. In other implementations, however, resetting a biometric performance measurement accumulation may cause the progress towards a biometric performance goal associated with the biometric performance measurement to be reset regardless of whether the goal achievement window for the biometric performance goal straddles the reset.

In some cases, the goal achievement window may, in effect, be infinite. For example, a biometric monitoring device may provide biometric performance goals that are triggered every time the total distance traveled (over the lifetime of the biometric monitoring device) reaches an even multiple of 1000 miles, regardless of how long it took the wearer to achieve the biometric performance goal.

In other implementations, the goal achievement window may be 1 hours, 8 hours, 1 day, 5 days, 1 week, or 1 month. In some implementations, the goal achievement window may be a 24-hour period starting and ending on midnight local time, a 7 day period starting or ending on a weekend, or a calendar month period.

The biometric performance goals may be provided without any input from the wearer of the device, e.g., provided as part of the original programming of the biometric monitoring device or uploaded to the biometric monitoring device by a third party, may be provided responsive to user-specified goals, e.g., the user may define a biometric performance goal of "take 5000 steps in 30 minutes," or may be provided using both techniques in combination. In many implementations, biometric performance goals may be specified using a device separate from the biometric monitoring device, e.g., a smartphone or a web server, and then communicated to the biometric monitoring device.

A biometric monitoring device may be configured to track multiple biometric performance goals simultaneously.

Biometric monitoring devices may be further configured to recognize completion of a biometric performance goal by presenting a special visual indicator on the display of the biometric monitoring device. The special visual indicator also may be referred to herein as a "goal celebration" or "goal celebration indicator." In some implementations, the goal celebration indicator may be auditory, e.g., a melody or sound effect, or tactile, e.g., a pattern of vibrations, and may not include any graphical content. Generally speaking, reference herein to a goal celebration indicator and display thereof may also be understood to refer to implementations that utilize non-visual goal celebration indicators (and in which the non-visual goal celebration indicators are provided using a mechanism other than a display, e.g., a speaker or vibramotor).

Such goal celebration indicators are distinct from the "normal" presentation of the biometric performance measurement data, i.e., they include content above and beyond, or in place of, typical numerical readouts of biometric performance measurement data. Goal celebration indicators may frequently be animated, and may serve as a visual celebration of the wearer's achievement of the biometric performance goal. For example, animations of fireworks going off, a smiling face, a "snake" that wiggles across display, and other types of animations may all be suitable goal celebration indicators. A particular biometric performance goal may have a specific goal celebration associated with it, or may select a goal celebration indicator from a number of potential goal celebration indicators associated with the biometric performance goal. In such instances, the particular goal celebration indicator may be randomly selected from the pool of potential goal celebration indicators, and/or may be selected according to certain predetermined rules.

In some implementations, the display of the goal celebration indicator may be somewhat decoupled from the achievement of the biometric performance goal. In such implementations, the display of the goal celebration indicator may be triggered only after the the biometric performance goal is met and after an input signal is subsequently received by the biometric monitoring device's processor(s). The input signal may, for example, be provided in response to a person's pushing of a button on the biometric monitoring device, or may be provided in response to other stimuli, e.g., biometric data indicating that the person has rotated their wrist in a manner similar to the motions made when a person checks the time on a wristwatch or biometric data indicating that the person is tapping on the housing of the biometric monitoring device. Such input signals are also discussed further in U.S. patent application Ser. No. 14/029,763, filed Sep. 17, 2013, which is hereby incorporated by reference in its entirety (this incorporated reference may refer to such signals as "user input").

Figure 3:
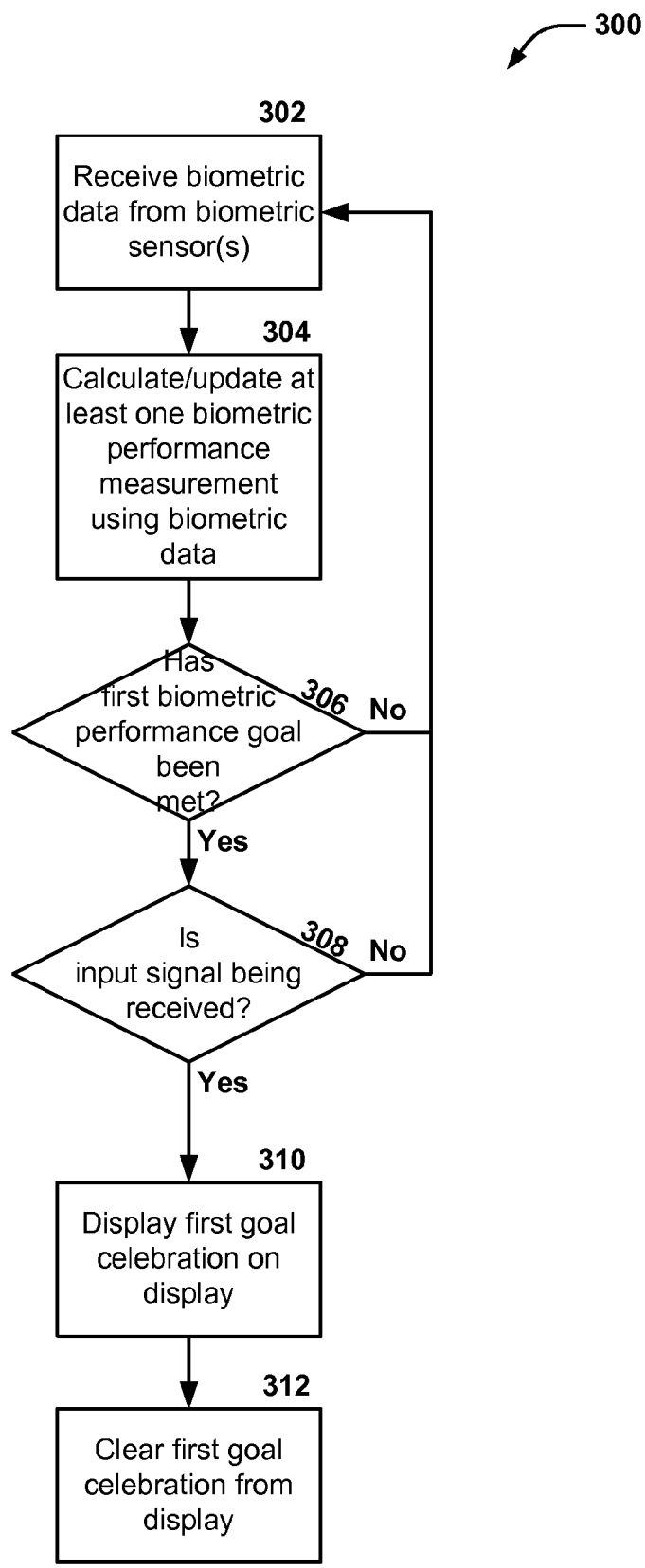
FIG. 3 depicts a flow diagram for a technique of incorporating delayed goal celebration in a biometric monitoring device.

FIG. 3 depicts a flow diagram for a technique of incorporating delayed goal celebration in a biometric monitoring device. In FIG. 3, biometric data may be received in block 302 by one or more processors of a biometric monitoring device from the biometric sensors of the biometric monitoring device. In block 304, the biometric data may be analyzed and used to calculate or update at least one biometric performance measurement, e.g., to calculate the number of steps taken, the distance traveled, the number of stair flights climbed, etc. In block 306, a determination may be made as to whether a first biometric performance goal has been reached. For example, the at least one biometric performance measurement may indicate that the wearer has walked 4999 steps during a first goal achievement window; if there is a first biometric performance goal of "walk 5000 steps," then the determination may be that the first biometric performance goal has not yet been met. In such a case, the technique may return to block 302, where further biometric data is received. The further biometric data may cause the at least one biometric performance measurement to be incremented or updated in block 304 such that a subsequent determination in block 306 as to whether the first biometric performance goal has been met is evaluated to be true, e.g. when the $5000^{th}$ step is taken in the above example, then the goal will have been met. If block 306 determines that the first biometric performance goal has been met, then the technique may advance to block 308, where a further determination may be made as to whether an input signal is being received (or has been received since block 306 was performed). If no input signal has been received, then the technique may return to block 302 for further biometric data collection. If block 308 determines that the input signal has been received, however, the technique may proceed to block 310, where a first goal celebration associated with the first biometric performance goal may be displayed on a display of the biometric monitoring device. In block 312, the first goal celebration may be cleared from the display, e.g., in response to a user input, time expiration, or other trigger. In some implementations, the first goal celebration may be retained in memory for some time and may be re-accessed by a wearer of the biometric monitoring device after displaying intervening content on the display.

It is to be understood that the display may, when not showing a goal achievement indicator, be either in an off or standby state or in an on state—when the goal achievement indicator is displayed, the display may, if in an off or standby state, be switched to an on state.

The present inventors have realized that biometric monitoring devices that are configured to delay display of earned goal celebration indicators until after the input signal is received may prove superior to biometric monitoring devices that immediately display a goal celebration indicator—such immediate-display biometric monitoring devices may display goal celebration indicators while the wearer is not paying attention, and the wearer may thus feel "cheated" of the reward of the goal celebration indicator. The present inventors have further realized that missing such acknowledgements of goal achievements may demoralize the wearer, and make them less likely to become invested in their fitness and health.

Figure 4:
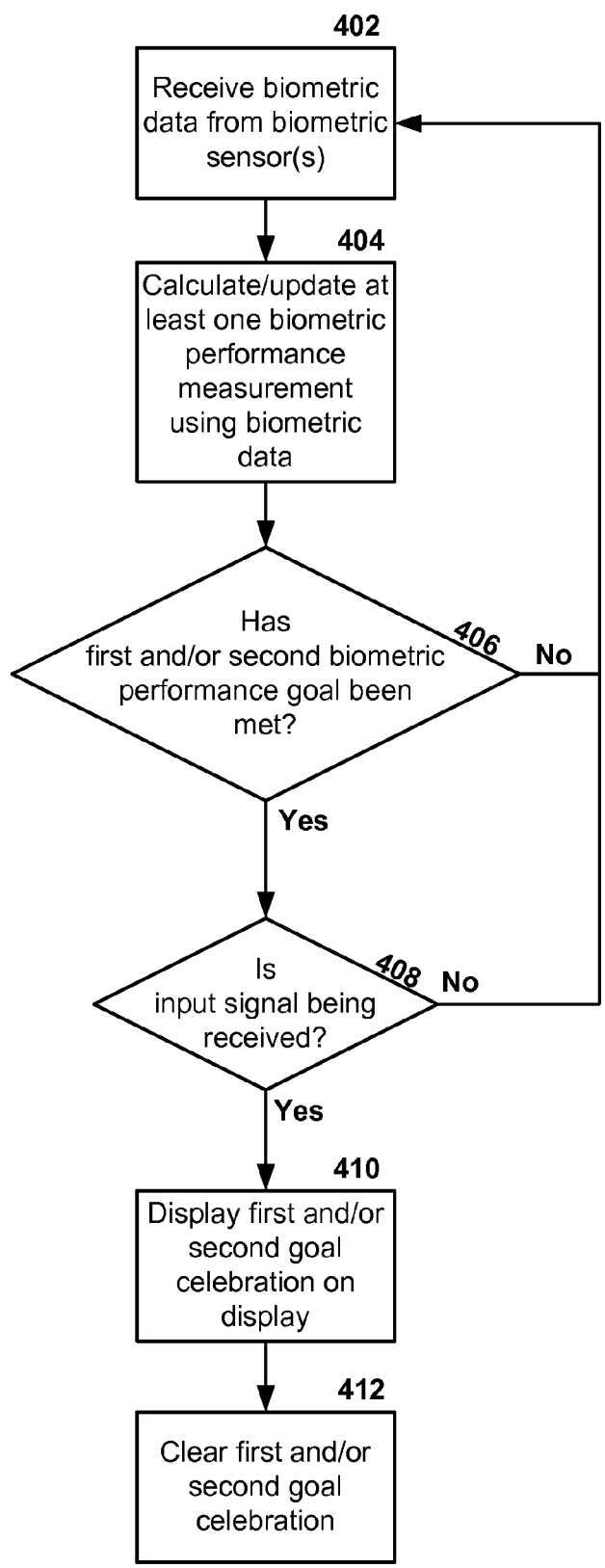
FIG. 4 depicts a flow diagram for a technique of incorporating delayed goal celebration in a biometric monitoring device for multiple biometric performance goals.

FIG. 4 depicts a flow diagram for a technique of incorporating delayed goal celebration in a biometric monitoring device for multiple biometric performance goals. FIG. 4 depicts a flow diagram for a technique of incorporating delayed goal celebration in a biometric monitoring device. In FIG. 4, biometric data may be received in block 402 by one or more processors of a biometric monitoring device from the biometric sensors of the biometric monitoring device. In block 404, the biometric data may be analyzed and used to calculate or update at least one biometric performance measurement, e.g., to calculate the number of steps taken, the distance traveled, the number of stair flights climbed, etc. In block 406, a determination may be made as to whether a first or second (or further additional) biometric performance goal has been reached. For example, the at least one biometric performance measurement may indicate that the wearer has walked 4999 steps during a first goal achievement window and that the wearer has climbed 10 flights of stairs during a second goal achievement window; if there is a first biometric performance goal of "walk 5000 steps" and a second biometric performance goal of "climb 10 flights of stairs," then the determination may be that the first biometric performance goal has not yet been met but that the second biometric performance goal has been met. If no biometric performance goals have been met, the technique may return to block 402, where further biometric data is received. The further biometric data may cause the at least one biometric performance measurement to be incremented or updated in block 404 such that a subsequent determination in block 406 as to whether the first or second biometric performance goal has been met is evaluated to be true. If block 406 determines that either the first or the second biometric performance goal has been met, then the technique may advance to block 408, where a further determination may be made as to whether an input signal is being received (or has been received since block 406 was performed). If no input signal has been received, then the technique may return to block 402 for further biometric data collection. If block 408 determines that the input signal has been received, however, the technique may proceed to block 410, where a first or second goal celebration associated with the first or second biometric performance goal may be displayed on a display of the biometric monitoring device. It is to be understood that multiple goal celebration indicators may be displayed, e.g., sequentially in order/reverse order of achievement, randomly, or in some other sequence, in cases where more than one biometric performance goal is met prior to the receipt of the input signal. In block 412, the first and/or second goal celebration indicator may be cleared from the display, e.g., in response to a user input, time expiration, or other trigger. In some implementations, the first and/or second goal celebrations may be retained in memory for some time and may be re-accessed by a wearer of the biometric monitoring device after displaying intervening content on the display.

Figure 5:
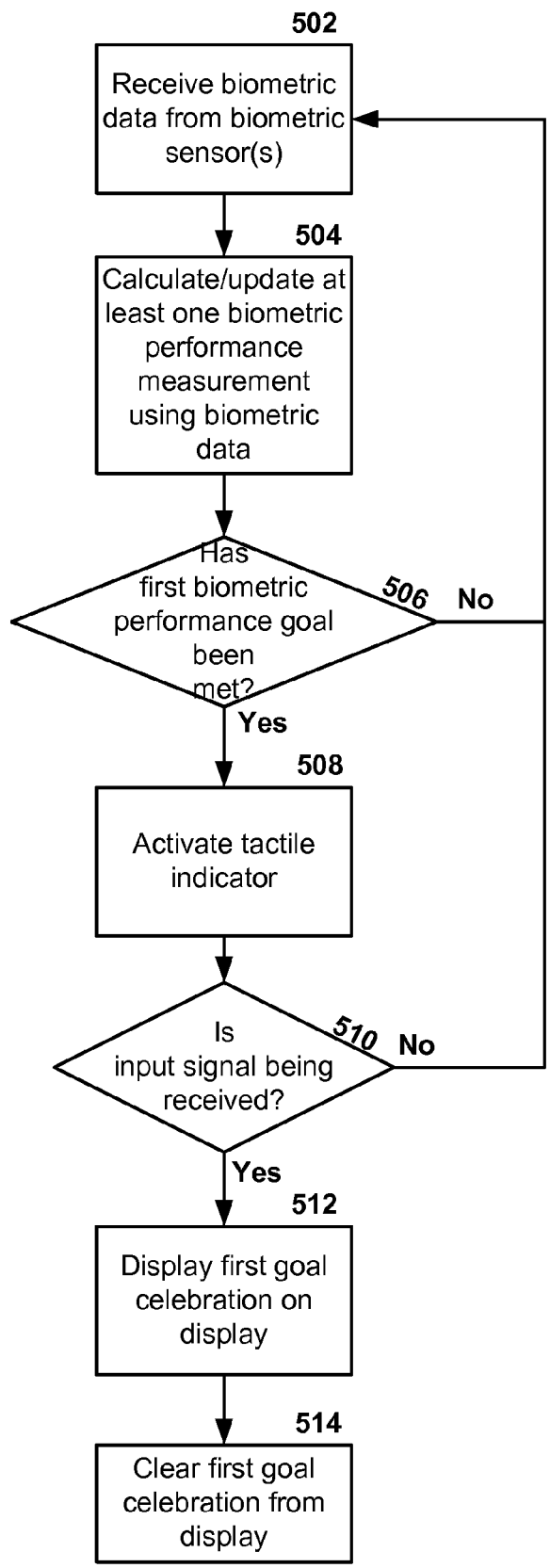
FIG. 5 depicts a flow diagram for a technique of incorporating delayed goal celebration in conjunction with immediate tactile feedback in a biometric monitoring device.

In some implementations, the techniques of FIGS. 3 and 4 may be modified to include a secondary form of indicating that a goal is met, e.g., a tactile feedback mechanism. FIG. 5 depicts a flow diagram for a technique of incorporating delayed goal celebration in conjunction with immediate tactile feedback in a biometric monitoring device. The technique in FIG. 5 is similar to the techniques of FIGS. 3 and 4. However, the technique of FIG. 5 also includes block 508, which is performed after block 506 (corresponding generally to block 306 and/or block 406) and before block 510 (corresponding generally to block 308 and/or 408. In block 506, a determination may be made as to whether or not a biometric performance goal (or goals) has been met. If it is determined in block 506 that a biometric performance goal has been met, the technique may proceed to block 508, where some form of secondary indicator, e.g., an audio signal like a chime, beep, melody, etc. or a tactile signal, e.g., vibration such as that produced by a small vibramotor or other vibratory device, may be used to alert the wearer of the biometric monitoring device that a biometric performance goal has been reached. Such secondary indicator may occur as soon as the biometric performance goal is reached, or shortly thereafter. The secondary indicator does not, however, require any input signal (such as may be determined in block 510) as is required for the delayed goal celebration indicator display. The secondary indicator may serve to alert the wearer that a goal has been achieved, and the wearer may then, at their leisure, trigger the display of any goal celebration indicators by providing the input signal to the biometric monitoring device. The technique may then continue to block 510 to determine if an input signal has been received; if not, the technique may return to block 502 and proceed through blocks 504 through 510 (although it is to be understood that block 508, and similar blocks in other techniques described herein, may be skipped for subsequent cycles once it has been performed for the completion of a particular biometric performance goal). If block 510 determines that the input signal has been received since the determination that the first biometric performance goal has been completed, then the technique may proceed to block 512, where a first goal celebration indicator associated with the biometric performance goal may be displayed. In block 514, the first goal celebration indicator may be cleared from the display.

It is to be understood that, in some implementations of the techniques described herein, there may be a timeout associated with a particular goal celebration indicator. For example, a biometric monitoring device (or other device that may present a goal celebration indicator, e.g., a laptop, tablet, or smartphone) may only show a goal celebration indicator in response to receiving the input signal within a certain period of time, e.g., 5 minutes, 15 minutes, 30 minutes, 1 hour, 1 day, etc., starting from when the corresponding biometric performance goal was met. For example, if the input signal is received within one hour of meeting the biometric performance goal, then the goal celebration indicator may be presented. However, if the input signal is received later than one hour after the biometric performance goal is met, then the goal celebration indicator may not be presented.

In many implementations, the secondary indicator and the goal celebration indicator may utilize different mediums, e.g., the goal celebration indicator may include graphics and sound, and the secondary indicator may be provided using tactile feedback (which may have some incidental audible components). In other implementations, the goal celebration indicator and the secondary indicator may both include graphical content.

Figure 6:
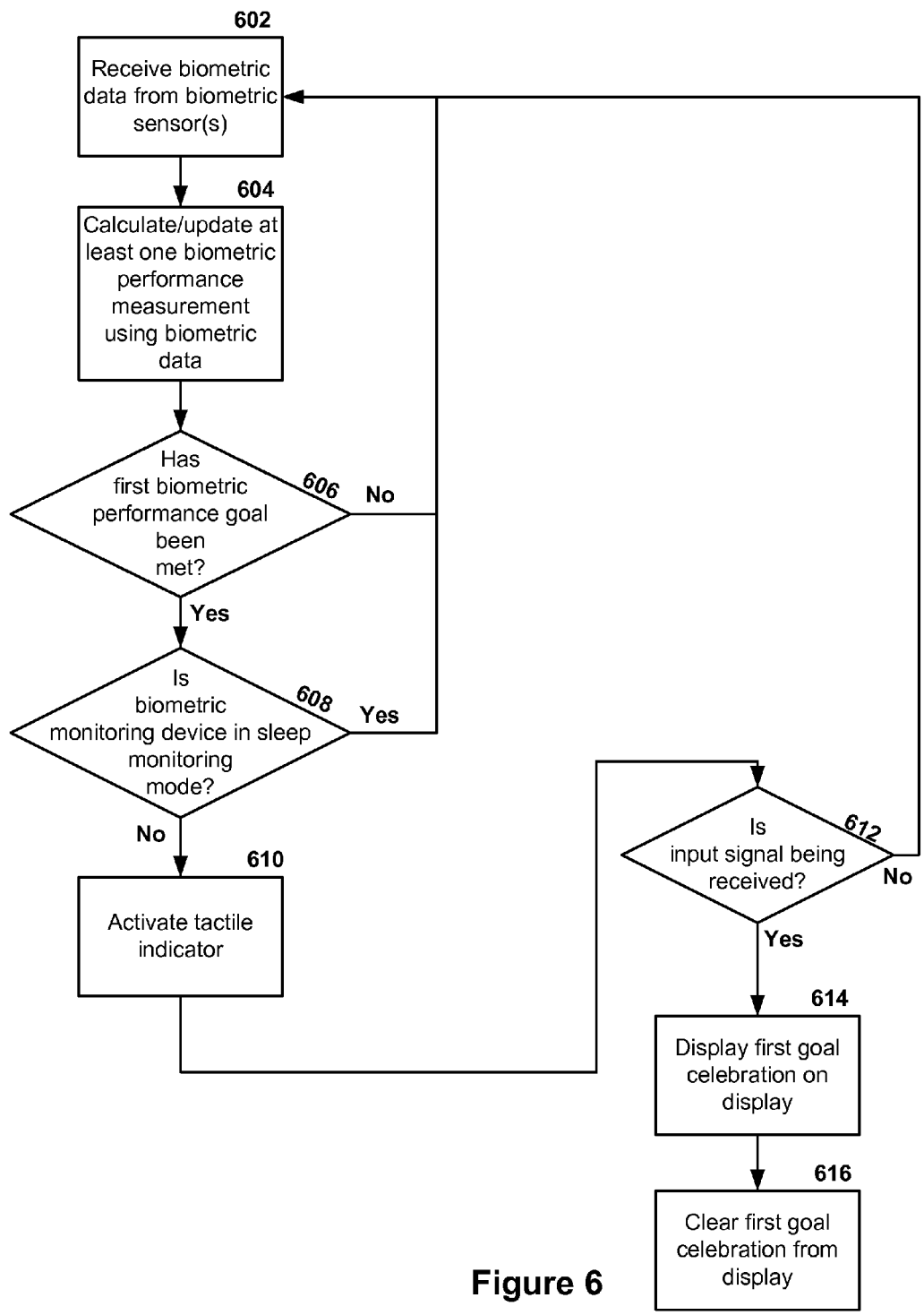
FIG. 6 depicts a flow diagram for a modified technique of incorporating delayed goal celebration in conjunction with immediate tactile feedback in a biometric monitoring device.

In some implementations, biometric monitoring devices such as those described herein may be configured to avoid providing a secondary indicator of goal completion in certain circumstances, such as when the wearer of the biometric monitoring device may be sleeping. FIG. 6 depicts a flow diagram for a modified technique of incorporating delayed goal celebration in conjunction with immediate tactile feedback in a biometric monitoring device.

In FIG. 6, biometric data may be received in block 602 by one or more processors of a biometric monitoring device from the biometric sensors of the biometric monitoring device. In block 604, the biometric data may be analyzed and used to calculate or update at least one biometric performance measurement. In block 606, a determination may be made as to whether a first biometric performance goal has been reached. If the determination of block 606 is negative, then the technique may return to block 602, where further biometric data may be received. If block 606 determines that the first biometric performance goal has been met, then the technique may advance to block 608, where a further determination may be made as to whether the biometric monitoring device is currently in a "sleep monitoring" mode. A sleep monitoring mode may be a user-activated, or automatically-activated, mode or environmental or contextual state that is intended to be active when the wearer is sleeping (or going to sleep). The sleep monitoring mode may serve as an indicator that there is a high likelihood that the wearer of the biometric monitoring device would be asleep or trying to sleep and would not wish to be disturbed, e.g., by a secondary indicator. In some implementations, the biometric monitoring device may not be in an "explicit" sleep mode such as the states described above, but may instead be in an "implicit" sleep mode—e.g., the biometric monitoring device may simply reference the time of day and, if the time of day falls between 9:00 PM and 8:00 AM, the biometric monitoring device may assume that this time frame is representative of a sleep cycle (without reference to any biometric data or user-activated mode). If the biometric monitoring device is determined to be in a sleep mode, then the technique may return to block 602 for further biometric data collection. If the biometric monitoring device is determined to not be in a sleep mode, then the technique may proceed to block 610, where a secondary indicator, e.g., audio or tactile indicator, may be activated to alert the wearer to the completion of a goal.

After the secondary indicator has been activated, the technique may proceed to block 612 for determination as to whether an input signal has been received. If block 612 determines that no input signal has been received, the technique may return to block 602. If block 612 determines that an input signal has been received after block 606 has determined that the first biometric performance goal has been met, then the technique may proceed to block 614, where a first goal celebration indicator may be displayed. Following the display of the first goal celebration indicator, block 616 may clear the first goal celebration indicator from the display.

Implementations using the technique of FIG. 6 may prove advantageous since they prevent the biometric monitoring device from inadvertently waking the wearer during sleep hours. The present inventors have also realized that such implementations also prevent the wearer from being alerted to the completion of an "activity" goal when the wearer is sedentary. For example, one example of a biometric performance goal may be to "burn 2000 calories in a day." A person may burn 1800 calories during the day, and may go to sleep prior to breaking the 2000 calorie mark. However, they will continue to burn calories while they are sleeping due to their basal metabolic rate (BMR), and the biometric monitoring device may determine that the 2000-calorie mark has been met while the person is asleep. If the person is woken from sleep to be told that they reached the 2000-calorie biometric performance goal, they may feel that the biometric monitoring data is inaccurate since they were not engaged in active activity when the biometric performance goal was reached (the person may not be aware of the effects of BMR). The implementation of FIG. 6 may help mitigate such situations.

The present inventors have also realized that it may be psychologically beneficial to restrict the notification of the wearer of a biometric monitoring device to completed biometric performance goals to times when the biometric monitoring device determines that an activity associated with the biometric performance goal is being performed. This is similar to the technique of FIG. 6, except that instead of evaluating whether the biometric monitoring device is in a sleep mode, the technique evaluates whether the biometric data indicates that a particular activity associated with a completed biometric performance goal is currently being performed. If so, then the technique may notify the wearer, e.g., via a secondary indicator, that a biometric performance goal has been met. If not, then the technique may wait until such an activity is detected and then notify the wearer of the biometric monitoring device using the secondary indicator.

Figure 7:
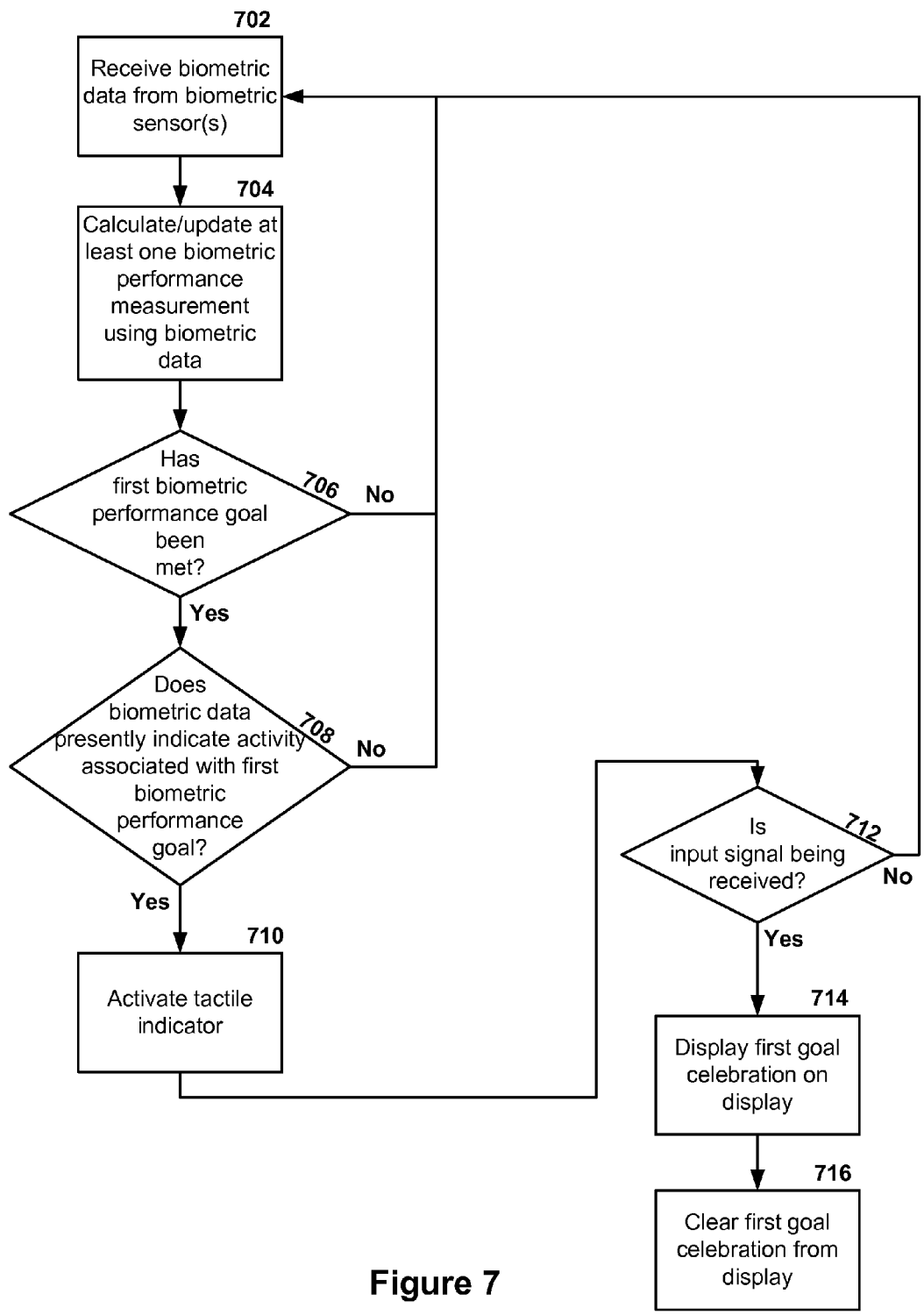
FIG. 7 depicts a flow diagram for another modified technique of incorporating delayed goal celebration in conjunction with activity-based tactile feedback in a biometric monitoring device.

FIG. 7 depicts a flow diagram for modified technique of incorporating delayed goal celebration in conjunction with activity-based tactile feedback in a biometric monitoring device. In FIG. 7, biometric data may be received in block 702 by one or more processors of a biometric monitoring device from the biometric sensors of the biometric monitoring device. In block 704, the biometric data may be analyzed and used to calculate or update at least one biometric performance measurement. In block 706, a determination may be made as to whether a first biometric performance goal has been reached. If the determination of block 706 is negative, then the technique may return to block 702, where further biometric data may be received. If block 706 determines that the first biometric performance goal has been met, then the technique may advance to block 708, where a further determination may be made as to whether the biometric monitoring device is currently in an activity mode that is associated with the first biometric performance goal. For example, if the first biometric performance goal is to "take 10,000 steps," then an activity mode that may be associated with the first biometric performance goal may be an activity mode such as walking or running (which may be determined based on accelerometer data indicating a certain frequency of steps over a given interval). The activity mode may, for example, require that a particular behavior continue uninterrupted for a certain period of time. For example, "walking" or "running" activity modes may only be engaged after biometric data indicating steps taken and spanning at least 10 continuous seconds is received by biometric monitoring device. The particular activity modes that may be evaluated in block 708 may be pre-set in association with the biometric performance goals, or may be selected based on the activity modes being triggered or otherwise associated with the biometric performance measurement(s) that is/are the subject of the first biometric performance goal.

If block 708 determines that a requisite activity mode is not active, then the technique may return to block 702 for further biometric data collection. If the biometric monitoring device is determined to be in a requisite activity mode, then the technique may proceed to block 710, where a secondary indicator, e.g., audio or tactile indicator, may be activated to alert the wearer to the completion of a goal. After the secondary indicator has been activated, the technique may proceed to block 712 for determination as to whether an input signal has been received. If block 712 determines that no input signal has been received, the technique may return to block 702. If block 712 determines that an input signal has been received after block 706 has determined that the first biometric performance goal has been met, then the technique may proceed to block 714, where a first goal celebration indicator may be displayed. Following the display of the first goal celebration indicator, block 716 may clear the first goal celebration indicator from the display.

Figure 8:
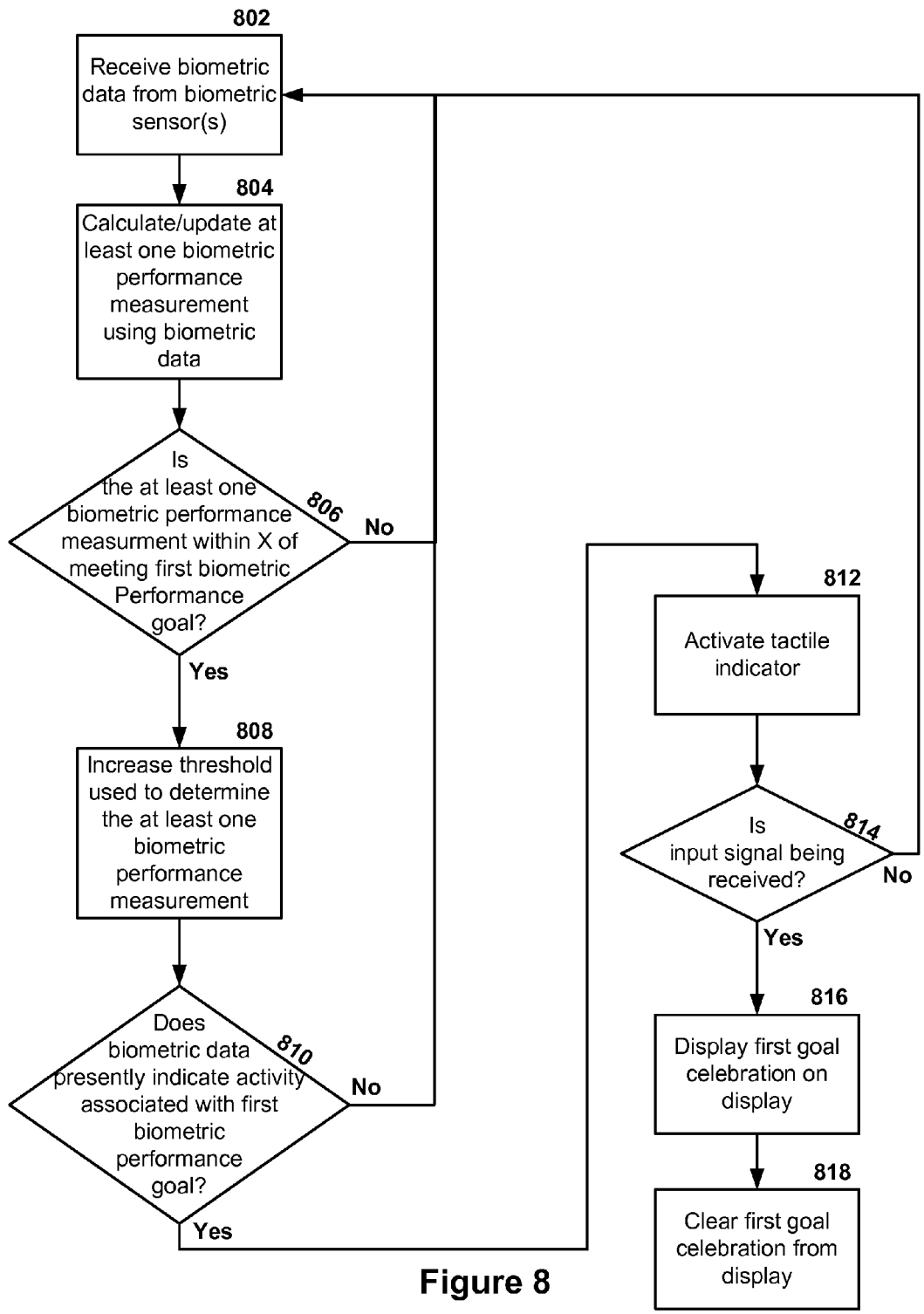
FIG. 8 depicts a flow diagram for a modified technique of fine-tuning goal completion determination in conjunction with delayed goal celebration.

In some implementations, the criteria used to determine biometric performance measurements may be fine-tuned prior to biometric performance goal completion. FIG. 8 depicts a flow diagram for a modified technique of fine-tuning goal completion determination in conjunction with delayed goal celebration.

In FIG. 8, biometric data may be received in block 802 by one or more processors of a biometric monitoring device from the biometric sensors of the biometric monitoring device. In block 804, the biometric data may be analyzed and used to calculate or update at least one biometric performance measurement. In block 806, a determination may be made as to whether the progress towards the first biometric performance goal is substantially complete. For example, such a determination may be percentage-based, e.g., determining whether the at least one biometric performance measurement is within some percentage of the first biometric performance goal. The percentage may be a relatively close percentage, e.g., within 90%, 95%, 99.9%, etc. In other implementations, the determination may be absolute, e.g., within some number of biometric performance measurement units of the first biometric performance goal. For example, when the at least one biometric performance measurement is within 1 to 20 units, e.g., stair flights, steps, calories burned, etc., of the first biometric performance goal, then the progress towards the first biometric performance goal may be deemed to be substantially complete. The selection of criteria for determining whether or not a biometric performance goal is "substantially complete" may be somewhat flexible, although it may generally be selected such that the maximum time it takes to actually complete the biometric performance goal as measured from the time when progress towards the biometric performance goal is deemed substantially complete may generally be on the order of seconds or tens of seconds.

If block 806 determines that progress towards the first biometric performance goal is not substantially complete, then the technique may return to block 802. If block 806 determines that progress towards the first biometric performance goal is substantially complete, however, then the technique may proceed to block 808, where a threshold that is used to determine if received biometric data is indicative of an increment or update to the at least one biometric performance measurement may be increased or made more stringent. For example, if the biometric performance measurement is "steps taken" and such a biometric performance measurement is determined by measuring the number of acceleration peaks that exceed particular thresholds in terms of magnitude and frequency, then a more stringent determination of the "steps taken" biometric performance measurement may increase the magnitude of the acceleration peaks by 10% and may increase the frequency that such peaks must have in order to be counted as "steps" by 50%. The technique may then proceed to block 810, in which a further determination may be made as to whether the biometric monitoring device is currently in an activity mode that is associated with the first biometric performance goal. If block 810 determines that a requisite activity mode is not active, then the technique may return to block 802 for further biometric data collection. If the biometric monitoring device is determined to be in a requisite activity mode, then the technique may proceed to block 812, where a secondary indicator, e.g., audio or tactile indicator, may be activated to alert the wearer to the completion of a goal. After the secondary indicator has been activated, the technique may proceed to block 814 for determination as to whether an input signal has been received. If block 814 determines that no input signal has been received, the technique may return to block 802. If block 814 determines that an input signal has been received after block 806 has determined that the first biometric performance goal has been met, then the technique may proceed to block 816, where a first goal celebration indicator may be displayed. Following the display of the first goal celebration indicator, block 818 may clear the first goal celebration indicator from the display. It is to be understood that blocks 810 and 812 may be omitted in some implementations, with block 808 leading directly to block 814, for example.

By tightening the thresholds for determining increments or updates to the at least one biometric performance measurement when the at least one biometric performance measurement nears a particular biometric performance goal, a biometric monitoring device may avoid or mitigate the appearance of "phantom" achievements. Biometric monitoring devices interpret biometric data according to various algorithms and attempt to transform such biometric data, which may include data such as accelerations, altitude, etc., into a biometric performance measurement. Due to noise in the data, algorithmic assumptions, and the limitations of the hardware used, there may be some error or looseness in the biometric performance measurements that are made. For example, the present inventors have realized that if a person is wearing a wrist-mounted biometric monitoring device while brushing their teeth, the up-and-down motion of the hand while holding the toothbrush might be accidentally interpreted as "steps" taken (even though the user may be standing still). The present inventors have further realized that such phantom data may cause a biometric performance goal to be achieved while the wearer of the biometric monitoring device is not performing any motion associated with the biometric performance goal. The present inventors have realized that by increasing the requirements for incrementing the biometric performance measurement in the last stages of biometric performance goal completion, the chances of phantom data driving the completion of biometric performance goals is reduced, and wearer confidence in the biometric monitoring device may be increased.

As discussed earlier, the input signals discussed with respect to the examples above may be any signal that indicates a user interaction with the biometric monitoring device, and may include, for example, input signals produced by buttons, touch-screen controls, voice commands, signals sent to the biometric monitoring device by an external device such as a smartphone, and input signals generated by the biometric monitoring device responsive to certain patterns of detected biometric data, e.g., biometric data indicative of a wrist-flick or tapping on the housing of the biometric monitoring device.

As discussed above, multiple biometric performance goals may be tracked simultaneously and multiple goal celebration indicators may have been accumulated prior to the receipt of the input signal. In such cases, a subset or all of the goal celebration indicators may be displayed, e.g., sequentially, upon receipt of the input signal.

In some implementations, the concepts discussed above may be implemented in various alternative/additional ways. For example, the secondary indicator, which may also be referred to herein as a "notification indicator" or the like (and which may be produced in response to receipt of a "notification signal" or the like), may be provided using graphical output, auditory output, tactile output (haptic output), or combinations thereof.

While the concepts described above are discussed with respect to an implementation in a single device, e.g., a biometric monitoring device, the concepts described herein may also be implemented so as to make use of multiple devices communicatively linked together into a system. For example, in some implementations, a biometric monitoring device may be paired with a smartphone that receives data from the biometric monitoring device. In such implementations, the first goal celebration indicator (or other goal celebration indicators) or the secondary indicator or notification indicator may be provided by the smartphone rather than by the biometric monitoring device (or in tandem with the biometric monitoring device). In addition to at least one biometric monitoring device, such a system may include, in general, one or more additional devices such as a smartphone, cell phone, tablet computer, laptop, desktop computer, or other electronic device capable of communicating with other devices in the system. For example, a biometric monitoring device may send biometric data back to a web server, e.g., Fitbit.com, where the biometric data may be analyzed to produce biometric performance measurements. The server (which may be one of the devices in the system) may then determine that a biometric performance goal has been met and may send information indicating that the biometric performance goal has been met to a computer associated with the biometric monitoring device (for example, a laptop that has software that can sync with the biometric monitoring device or a desktop that is used to access a web-based portal to a user account associated with the biometric monitoring device); the computer may then, in response to receiving such an indication and in response to some other stimulus, e.g., launching an application associated with the biometric monitoring device, turning on the computer, or logging in to a website account associated with the biometric monitoring device, may present a goal celebration indicator.

Regardless of which device in such a multi-component system provides a goal celebration indicator or secondary indicator/notification indicator, it is to be understood that the goal celebration indicator is triggered after the associated goal is met and in response to an input signal, e.g., a button push, wrist flick, etc. Accordingly, the goal celebration indicator may be substantially decoupled in time from the point at which the associated biometric performance goal is actually met. In contrast, the secondary indicator/notification indicator may occur as soon as the associated biometric performance goal is met (and without waiting for the input signal). Thus, the secondary indicator/notification indicator may act to alert a wearer of the biometric monitoring device that a goal has been met, and may do so substantially concurrently with the actual attainment of the biometric performance goal. By contrast, the goal celebration indicator associated with that biometric performance goal may be "held in reserve" until the wearer indicates, via the input signal, that they are ready to be presented with the goal celebration indicator. In this way, the wearer is kept more engaged with the attainment/non-attainment of biometric performance goals since they are reassured that they will not miss a goal celebration indicator through inattentiveness. Such distinctions are applicable regardless of which device presents the goal celebration indicator and/or the secondary indicator/notification indicator. In many implementations, the notification indicators may be considerably less elaborate than the goal celebration indicators. Furthermore, in some implementations, the notification indicators may be the same for all or a subset of biometric performance goals, e.g., a vibrational pulse may be used to indicate the attainment of a biometric performance goal regardless of which biometric performance goal it is. In such implementations, each biometric performance goal may be associated with the same notification indicator. In other implementations, however, different biometric performance goals may be associated with different notification indicators.

It is to be understood that in multi-component systems, the various actions taken to perform the concepts outlined herein may be performed in a distributed manner. For example, a biometric monitoring device may be configured to collect biometric data and transmit the biometric data to a paired smartphone. The smartphone may then analyze the biometric data to determine a biometric performance measurement and may then determine whether or not a first biometric performance goal has been reached (of course, the biometric monitoring device may also perform these tasks, as discussed with respect to the earlier examples herein). The smartphone may then notify the biometric monitoring device that the first biometric performance goal has been met, and the biometric monitoring device may vibrate to alert the wearer that the first biometric performance goal has been met (a notification indicator). In such an implementation, the smartphone may be configured to provide an associated goal celebration indicator (rather than, or in addition to, a goal celebration indicator presented by the biometric monitoring device). Alternatively or additionally, the smartphone may provide both the secondary indicator and the goal celebration indicator. In some other or additional implementations, the smartphone may provide the secondary indicator and the goal celebration may be provided by the biometric monitoring device.

To assist in discussion of such multi-component systems, the term "output signal" may be used—an output signal is to be understood to refer to a signal that is generated in response to the receipt of an input signal and after a determination has been made that a biometric performance goal has been met. The output signal may, for example, be a signal sent to a display device of a biometric monitoring device that causes the display to present a goal celebration indicator (or to a tactile actuator to cause the tactile actuator to present a goal celebration indicator, or to an audio device to cause the audio device to present a goal celebration indicator). The output signal may, alternatively or additionally, be a signal, for example, that is transmitted by a biometric monitoring device via a wireless communications interface to a smartphone. The smartphone, on receipt of the output signal, may then display a goal celebration indicator.

The term "input signal" may be used to indicate a signal that is indicative of a user interaction with a biometric monitoring device or with a smartphone or other device. In the context of this disclosure, the term "input signal" is to be further understood to refer to signals that are indicative of actions taken by a user in order to have goal celebration indicators presented.

The term "notification signal" may be used to indicate a signal that causes a notification indicator to be presented. As with the output signal, the notification signal may be internal to a single device, e.g., originate within a biometric monitoring device and cause a device within the biometric monitoring device to present the notification indicator, or may be transmitted to another device, e.g., to a smartphone, to cause the other device to present the notification indicator.

Generally speaking, the calculations and determinations discussed herein may be performed in various locations within a system, e.g., by processors of a biometric monitoring device, processors of a smartphone, processors of a web server, or combinations thereof. Moreover, the computer-executable instructions for performing the techniques outlined herein in the context of a multi-component system may be stored in memories associated with each involved component; each component, however, may only store instructions that are relevant to that component's role in performing the techniques discussed herein. A complete set of the instructions may, however, be found in aggregate when one considers the memories of the multiple components that are involved in providing the techniques discussed herein in the context of a multi-component system.

In some implementations, the smartphone may act as a relay between the biometric monitoring device and a remote server, and the remote server may evaluate the biometric data to determine biometric performance measurements and whether or not a particular biometric performance goal has been met. The remote server may then send output signals and/or notification signals to a smartphone or to the biometric monitoring device to cause the receiving device to present a goal celebration indicator or notification indicator.

In some implementations, the notification signal may be generated by one device, e.g., the biometric monitoring device, and sent to another device, e.g., a smartphone. The smartphone, upon receiving the notification signal, may present a notification indicator. The smartphone may also (after receiving the notification signal) await an input signal and, upon receipt, may then generate an output signal associated with the biometric performance goal with which the notification signal was associated.

It is to be understood that while the above examples refer to "smartphones," such examples may also be implemented using other electronic devices other than smartphones, e.g., tablet computers, laptops, PDAs, desktop computers, etc., and that such alternative implementations are also considered to be within the scope of this disclosure.

There are many biometric sensors that may be used to detect various types of biometric data that may determine, at least in part, biometric performance measurements. The biometric sensors may include one or more sensors that evaluate a physiological aspect of a wearer of the device, e.g., heart rate sensors, galvanized skin response sensors, skin temperature sensors, electromyography sensors, etc. The biometric sensors may also or alternatively include sensors that measure physical environmental characteristics that reflect how the wearer of the device is interacting with the surrounding environment, e.g., accelerometers, altimeters, GPS devices, gyroscopes, etc. All of these are biometric sensors that may all be used to gain insight into the activities of the wearer, e.g., by tracking movement, acceleration, rotations, orientation, altitude, etc.

A larger listing of potential biometric sensor types and/or biometric data types is shown below in Table 1. This listing is not exclusive, and other types of biometric sensors other than those listed may be used. Moreover, the data that is potentially derivable from the listed biometric sensors may also be derived, either in whole or in part, from other biometric sensors. For example, an evaluation of stairs climbed may involve evaluating altimeter data to determine altitude change, clock data to determine how quickly the altitude changed, and accelerometer data to determine whether biometric monitoring device is being worn by a person who is walking (as opposed to standing still).

TABLE 1

| Biometric Sensor Type | Biometric data potentially measured | Potentially derivable biometric data |
|---|---|---|
| Accelerometers | Accelerations experienced at location worn | Rotation, translation, velocity/speed, distance traveled, steps taken, elevation gained, fall indications, calories burned (in combination with data such as user weight, stride, etc.) |
| Gyroscopes | Angular orientation, angular velocity, angular acceleration and/or rotation | Rotation, orientation |
| Altimeters | Barometric pressure, temperature (to calculate a more accurate altitude) | Altitude change, flights of stairs climbed, local pressure changes, submersion in liquid |
| Pulse Oximeters | Blood oxygen saturation (SpO2), heart rate, blood volume | Heart rate variability, stress levels, active heart rate, resting heart rate, sleeping heart rate, sedentary heart rate, cardiac arrhythmia, cardiac arrest, pulse transit time, heart rate recovery time, blood volume |
| Galvanic Skin Response Sensors | Electrical conductance of skin | Perspiration, stress levels, exertion/arousal levels |
| Global Positioning System (GPS) | Location, elevation, speed, heading | Distance traveled, velocity/speed |
| Electromyographic Sensors | Electrical pulses | Muscle tension/extension |
| Audio Sensors | Local environmental sound levels | Laugh detection, breathing detection, snoring detection, respiration type (snoring, breathing, labored breathing, gasping), voice detection, typing detection |
| Photo/Light Sensors | Ambient light intensity, ambient light wavelength | Day/night, sleep, UV exposure, TV watching, indoor v. outdoor environment |
| Temperature Sensors | Temperature | Body temperature, ambient environment temperature |
| Strain Gauge Sensors | Weight (the strain gauges may be located in a device remote from the biometric monitoring device, e.g., a Fitbit Aria ™ scale, and communicate weight-related data to the biometric monitoring device, either directly or via a shared account over the Internet) | Body Mass Index (BMI) (in conjunction with user-supplied height and gender information, for example) |
| Bioelectrical Impedance Sensors | Body fat percentage (may be included in remote device, such as Aria ™ scale) | |
| Respiration Rate Sensors | Respiration rate | Sleep apnea detection |
| Blood Pressure Sensors | Systolic blood pressure, diastolic blood pressure | |
| Heart Rate Sensors | Heart rate | |
| Blood Glucose Sensors | Blood glucose levels | |
| Moisture Sensors | Moisture levels | Whether user is swimming, showering, bathing, etc. |

In addition to the above, some biometric data may be calculated by the biometric monitoring device without direct reference data obtained from the biometric sensors. For example, a person's basal metabolic rate, which is a measure of the "default" caloric expenditure that a person experiences throughout the day while at rest (in other words, simply to provide energy for basic bodily functions such as breathing, circulating blood, etc.), may be calculated based on data entered by the user and the used, in conjunction with data from an internal clock indicating the time of day, to determine how many calories have been expended by a person thus far in the day just to provide energy for basic bodily functions.

As discussed above, one or more of the biometric sensors discussed herein may be used to detect a physical gesture corresponding to a user input and may, in response, generate an input signal. This allows a user to interact with the device using physical gestures. For example, a wrist-based portable biometric device may contain an accelerometer, magnetometer (which may be used to detect the biometric monitoring device's orientation with respect to the Earth's magnetic field), and/or a gyroscope. One or more of these sensors may be used to determine when the user moves their wrist in a manner that is similar to that performed when viewing a watch. The portable biometric device may interpret this gesture as a user input or interaction and generate the input signal in response. Other gestures that may be interpreted to provide the input signal include, but are not limited to, multiple taps, or a specific pattern of taps. For example, a user may tap anywhere on the exterior of the portable biometric monitoring device two times within a specific time period, e.g., one second, to generate the input signal.

In another embodiment, a wrist-based portable biometric device may have one or more electromyographic (EMG) sensors in the band. These EMG sensors may detect when the user flexes the muscles in their forearm/wrist by forming a fist, for example. This gesture may be interpreted by the portable biometric device as a user input that causes input signal. While some physical gestures are provided here to illustrate gesture based interactions, these examples should not be considered exhaustive.

It is to be understood that there may be a variety of techniques in addition to those described herein that may be used to implement delayed goal celebration as described herein; such additional techniques are also considered within the scope of this disclosure.

Generally speaking, the techniques and functions outlined above may be implemented in a biometric monitoring device as machine-readable instruction sets, either as software stored in memory, as application-specific integrated circuits, field-programmable gate-arrays, or other mechanisms for providing system control. Such instruction sets may be provided to a processor or processors of a biometric monitoring device to cause the processor or processors to control other aspects of the biometric monitoring device to provide the functionality described above.

Unless the context (where the term "context" is used per its typical, general definition) of this disclosure clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also generally include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list, and any combination of the items in the list. The term "implementation" refers to implementations of techniques and methods described herein, as well as to physical objects that embody the structures and/or incorporate the techniques and/or methods described herein.

It is to be understood that the use of ordinal indicators, e.g., a), b), c) . . . or the like, does not inherently convey any particular order of operations, but is merely used as a convenient mechanism for referencing different operations or steps of a technique.

The phrase "responsive to" is to be understood to refer to an action or step that is performed relatively immediately after a particular other action or step, at least from the perspective of a human observer. For example, if a person presses a button on an example biometric monitoring device and the display of the biometric monitoring device turns on immediately afterwards in response, then the activation of the display may be said to be "responsive to" the receipt of a signal from the button (indicating that the button has been pressed). There may, of course, be some small delay between the receipt of such a signal and the performance of the follow-on action, e.g., due to computational delays, but, generally speaking, such follow-on actions occur either immediately or shortly after the triggering action, i.e., on the order of seconds or less after.

There are many concepts and implementations described and illustrated herein. While certain features, attributes and advantages of the implementations discussed herein have been described and illustrated, it should be understood that many others, as well as different and/or similar implementations, features, attributes and advantages of the present inventions, are apparent from the description and illustrations. As such, the above implementations are merely exemplary. They are not intended to be exhaustive or to limit the disclosure to the precise forms, techniques, materials and/or configurations disclosed. Many modifications and variations are possible in light of this disclosure. It is to be understood that other implementations may be utilized and operational changes may be made without departing from the scope of the present disclosure. As such, the scope of the disclosure is not limited solely to the description above because the description of the above implementations has been presented for the purposes of illustration and description.

Importantly, the present disclosure is neither limited to any single aspect nor implementation, nor to any single combination and/or permutation of such aspects and/or implementations. Moreover, each of the aspects of the present disclosure, and/or implementations thereof, may be employed alone or in combination with one or more of the other aspects and/or implementations thereof. For the sake of brevity, many of those permutations and combinations will not be discussed and/or illustrated separately herein.

What is claimed is:

1. A system comprising:
   a biometric monitoring device having:
     one or more biometric sensors,
     at least one processor,
     a communications interface, and
     a memory, wherein:
       the memory, the at least one processor, the communications interface, and the one or more biometric sensors are communicatively connected with one another; and
       the memory stores computer-executable instructions for controlling the at least one processor to:
         a) receive biometric data from the one or more biometric sensors,
         b) calculate at least one biometric performance measurement using the biometric data,
         c) determine at a first time that the at least one biometric performance measurement indicates that a first biometric performance goal has been met during a first goal achievement window,
         d) determine, after c), that at least one first activity mode associated with the first biometric performance goal is indicated as active by the biometric data for at least a first interval of time, wherein c) occurs before or during the first interval of time, and
         e) transmit a first output signal associated with the first biometric performance goal via the communications interface after c) and responsive to d); and
   a mobile communications device separate from the biometric monitoring device, the mobile communications device having:
     at least one mobile communications device processor,
     a mobile communications device memory,
     a mobile communications device display, and
     a mobile communications device communications interface, wherein:
       the at least one mobile communications device processor, the mobile communications device memory, the mobile communications device display, and the mobile communications device communications interface are communicatively connected with one another; and
       the mobile communications device memory stores computer-executable instructions for controlling the at least one mobile communications device processor to:

f) receive the first output signal transmitted from the communications interface of the biometric monitoring device in d), and g) cause, responsive at least in part to f) and after e), the mobile communications device display to produce a first goal celebration indicator associated with the first biometric performance goal.

2. The system of claim 1, wherein g) further comprises causing the mobile communications device display to turn on from an off or standby state before producing a first goal celebration indicator associated with the first biometric performance goal.

3. The system of claim 1, wherein the computer-executable instructions further include instructions for:

h) controlling the at least one mobile communications device processor to receive a first input signal, and controlling the at least one mobile communications device processor to perform g) responsive to f) and h), wherein the first input signal is generated by the mobile communications device responsive to the at least one mobile communications device processor detecting an action selected from the group consisting of: powering on the mobile communications device from an off state, transitioning the mobile communications device from a standby state to an on state, activating a software program associated with the biometric monitoring device, pushing a button on the mobile communications device, selecting a touch-screen control on the mobile communications device, receiving a communication from the biometric monitoring device via the mobile device communications interface, and combinations thereof.

4. The system of claim 3, wherein the mobile communications device memory stores further computer-executable instructions for controlling the at least one mobile communications device processor to:

i) cause a secondary indicator to be generated responsive to f) and independently of h), wherein the secondary indicator indicates that a first biometric performance goal has been reached and that the associated first goal celebration indicator will be displayed responsive to an interaction of a person with the mobile communications device.

5. The system of claim 4, wherein the secondary indicator is selected from the group consisting of: a display of graphical content on the mobile communications device display, tactile feedback provided by a haptic mechanism of the mobile communications device, audio output provided by an audio device of the mobile communications device, and combinations thereof.

6. The system of claim 4, wherein the first biometric performance goal and the associated first goal celebration indicator are unidentifiable based on the secondary indicator.

7. The system of claim 3, wherein g) further comprises receiving the first input signal during a first input signal window.

8. The system of claim 7, wherein the first input signal window is a time period less than 1 day after the at least one processor determines that the first biometric performance goal has been met in c).

9. The system of claim 1, wherein the first goal celebration indicator is selected from the group consisting of: a display of graphical content on the mobile communications device display, tactile feedback provided by a haptic mechanism of the mobile communications device, audio output provided by an audio device of the mobile communications device, and combinations thereof.

10. The system of claim 1, wherein:

the mobile communications device memory stores further computer-executable instructions for controlling the at least one mobile communications device processor to:

h) receive a first input signal;

i) cause a secondary indicator to be generated responsive to f) and independently of h), wherein the secondary indicator indicates that a first biometric performance goal has been reached and that a second goal celebration indicator will be displayed on a biometric monitoring device display of the biometric monitoring device responsive to an interaction of a person with the biometric monitoring device; and the biometric monitoring device further comprises the biometric monitoring device display and the memory stores further computer-executable instructions for controlling the at least one processor to:

j) receive a second input signal indicative of a user interaction with the biometric monitoring device, and k) responsive to j) and after i), cause the biometric monitoring device display to produce the second goal celebration indicator associated with the first biometric performance goal.

11. The system of claim 1, wherein:

the memory stores further computer-executable instructions for controlling the at least one processor to:

h) determine at a second time that the at least one biometric performance measurement indicates that a second biometric performance goal different from the first biometric performance goal has been met during a second goal achievement window, and i) transmit a second output signal associated with the second biometric performance goal via the communications interface after h); and the mobile communications device memory stores further computer-executable instructions for controlling the at least one mobile communications device processor to:

k) receive the second output signal transmitted from the biometric monitoring device in m), and l) cause, responsive at least in part to k) and after h), cause the mobile communications device to produce a second goal celebration indicator associated with the second biometric performance goal.

12. The system of claim 11, wherein the second biometric performance goal includes a plurality of different biometric performance goals and the second biometric performance goal is met by meeting any one of the biometric performance goals in the plurality of different biometric performance goals.

13. The system of claim 11, wherein the first goal celebration indicator and the second goal celebration indicator are different goal celebration indicators.

14. The system of claim 1, wherein the mobile communications device is a device selected from the group consisting of: smartphones, cellphones, tablet computers, and laptops.

15. The system of claim 1, wherein the first goal celebration indicator is selected from a plurality of goal celebrations associated with the first biometric performance goal.

16. The system of claim 15, wherein the first goal celebration indicator is selected from the plurality of goal celebrations according to a set of predetermined goal celebration selection rules.

17. The system of claim 16, wherein the set of predetermined goal celebration selection rules cause the first goal celebration to be selected responsive to a goal celebration choice from a user.

18. The system of claim 15, wherein the first goal celebration indicator is randomly selected from the plurality of goal celebrations.

19. The apparatus of claim 1, wherein the first interval of time is at least 10 continuous seconds and the biometric data indicates that the first activity mode is active in an uninterrupted state for the first interval of time.

20. The apparatus of claim 1, wherein the first activity mode is selected from the group consisting of walking and running and the biometric performance measurement is steps taken.

21. A system comprising:
a biometric monitoring device having:
one or more biometric sensors,
at least one processor,
a communications interface, and
a memory, wherein:
the memory, the at least one processor, the communications interface, and the one or more biometric sensors are communicatively connected with one another, and
the memory stores computer-executable instructions for controlling the at least one processor to:
a) receive biometric data from the one or more biometric sensors; and
at least one remote device separate from the biometric monitoring device, the at least one remote device including at least one remote device processor, a remote device communications interface, and a remote device memory, wherein:
the remote device memory, the at least one remote device processor, and the remote device communications interface are communicatively connected with one another,
the biometric monitoring device and the at least one remote device further include, in aggregate, a display, and
the memory and the at least one remote device memory store, in aggregate, computer-executable instructions for controlling the system to:
b) calculate at least one biometric performance measurement using the biometric data;
c) determine that a first biometric performance goal has been met based on the at least one biometric performance measurement;
d) determine, after c), that at least one first activity mode associated with the first biometric performance goal is indicated as active by the biometric data for at least a first interval of time, wherein c) occurs before or during the first interval of time;
e) provide, responsive to d) and after c), a notification indicator that the first biometric performance goal has been met;
f) receive an input signal indicating a user interaction with an item selected from the group consisting of the biometric monitoring device and the at least one remote device; and
g) responsive to f) and after c), cause the display to produce a first goal celebration indicator associated with the first biometric performance goal.

22. The system of claim 21, wherein the first goal celebration indicator is selected from the group consisting of: a graphical display of visual elements associated with meeting the biometric performance goal, audible sounds associated with meeting the biometric performance goal, tactile feedback associated with meeting the biometric performance goal, and combinations thereof.

23. The apparatus of claim 21, wherein the first interval of time is at least 10 continuous seconds and the biometric data indicates that the first activity mode is active in an uninterrupted state for the first interval of time.

24. The apparatus of claim 21, wherein the first activity mode is selected from the group consisting of walking and running and the biometric performance measurement is steps taken.

25. A system comprising:
a biometric monitoring device having:
one or more biometric sensors,
at least one processor,
a communications interface, and
a memory, wherein:
the memory, the at least one processor, the communications interface, and the one or more biometric sensors are communicatively connected with one another, and
the memory stores computer-executable instructions for controlling the at least one processor to:
a) receive biometric data from the one or more biometric sensors;
a first remote device including a first remote device processor, a first remote device communications interface, and a first remote device memory, wherein:
the first remote device memory, the first remote device processor, and the first remote device communications interface are communicatively connected with one another; and
a second remote device including a second remote device processor, a second remote device communication interface, and a second remote device memory, wherein:
the second remote device memory, the second remote device processor, and the second remote device communications interface are communicatively connected with one another,
at least one of the biometric monitoring device, the first remote device, and the second remote device further includes a display,
the memory, the first remote device memory, and the second remote device memory store, in aggregate, computer-executable instructions for controlling the system to:
b) calculate at least one biometric performance measurement using the biometric data;
c) determine that a first biometric performance goal has been met based on the at least one biometric performance measurement;
d) determine, after c), that at least one first activity mode associated with the first biometric performance goal is indicated as active by the biometric data for at least a first interval of time, wherein c) occurs before or during the first interval of time;
e) transmit a first output signal associated with the first biometric performance goal via the first remote device communications interface after c) and responsive to d);
f) receive the first output signal transmitted from the first remote device in e);
g) receive a first input signal; and
h) responsive to g) and after f), cause the display to produce a first goal celebration indicator associated with the first biometric performance goal.

26. The apparatus of claim 25, wherein the first interval of time is at least 10 continuous seconds and the biometric data indicates that the first activity mode is active in an uninterrupted state for the first interval of time.

27. The apparatus of claim 25, wherein the first activity mode is selected from the group consisting of walking and running and the biometric performance measurement is steps taken.

* * * * *